United States Patent
Hollis et al.

(10) Patent No.: US 10,582,957 B2
(45) Date of Patent: Mar. 10, 2020

(54) BONE FIXATION IMPLANT AND MEANS OF FIXATION

(71) Applicant: CROSSROADS EXTREMITY SYSTEMS, LLC, Memphis, TN (US)

(72) Inventors: Michael Hollis, Collierville, TN (US); Vernon Hartdegen, Collierville, TN (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 0 days.

(21) Appl. No.: 15/512,499

(22) PCT Filed: Sep. 10, 2015

(86) PCT No.: PCT/US2015/049359
§ 371 (c)(1),
(2) Date: Mar. 17, 2017

(87) PCT Pub. No.: WO2016/044053
PCT Pub. Date: Mar. 24, 2016

(65) Prior Publication Data
US 2017/0245902 A1    Aug. 31, 2017

Related U.S. Application Data

(60) Provisional application No. 62/052,531, filed on Sep. 19, 2014.

(51) Int. Cl.
*A61B 17/72* (2006.01)
*A61B 17/16* (2006.01)
(Continued)

(52) U.S. Cl.
CPC ...... *A61B 17/7291* (2013.01); *A61B 17/1686* (2013.01); *A61B 17/7233* (2013.01);
(Continued)

(58) Field of Classification Search
CPC ............ A61B 17/7291; A61B 17/1668; A61B 17/7233; A61B 2017/044
See application file for complete search history.

(56) References Cited

U.S. PATENT DOCUMENTS 4,997,433 A    3/1991  Goble
5,053,035 A *  10/1991 McLaren ........... A61B 17/7208
                                                606/62
(Continued)

FOREIGN PATENT DOCUMENTS

AU    200013505    4/2000
BR    MU9000145    1/2012
(Continued)

*Primary Examiner* — Jan Christopher L Merene
(74) *Attorney, Agent, or Firm* — Maywood IP Law; G. Jo Hays; David W. Meibos

(57) ABSTRACT

An implant for osteosynthesis which can be used to repair fractures and or fuse joints. The implant comprises one or more through holes for the passage of one or more sutures therethrough and or one or more sutures may be an integral part of the implant. The one or more sutures may be used to pull bone segments together and create compression therebetween and or to affix soft tissue to a bone segment.

21 Claims, 16 Drawing Sheets

(51) Int. Cl.
*A61B 17/88* (2006.01)
*A61B 17/84* (2006.01)
*A61B 90/00* (2016.01)

(52) U.S. Cl.
CPC ........ *A61B 17/848* (2013.01); *A61B 17/8861* (2013.01); *A61B 17/8872* (2013.01); *A61B 2090/036* (2016.02); *A61B 2090/037* (2016.02); *A61B 2090/062* (2016.02)

(56) References Cited

U.S. PATENT DOCUMENTS

| | | | |
|---|---|---|---|
| 5,102,421 | A | 4/1992 | Anspach, Jr. |
| 5,306,290 | A | 4/1994 | Martins |
| 5,336,240 | A | 8/1994 | Metzler |
| 5,370,662 | A | 12/1994 | Stone |
| 5,522,843 | A | 6/1996 | Zang |
| 5,534,011 | A | 7/1996 | Greene, Jr. |
| 5,571,139 | A | 11/1996 | Jenkins, Jr. |
| 5,573,548 | A | 11/1996 | Nazre |
| 5,584,836 | A | 12/1996 | Ballintyn |
| D385,352 | S | 10/1997 | Bales |
| 5,697,950 | A | 12/1997 | Fucci |
| 5,766,174 | A | 6/1998 | Perry |
| 5,851,219 | A | 12/1998 | Goble |
| 5,904,704 | A | 5/1999 | Goble |
| 5,957,924 | A | 9/1999 | Tormala |
| 5,961,524 | A | 10/1999 | Crombie |
| 5,964,783 | A | 10/1999 | Grafton |
| 6,019,768 | A | 2/2000 | Wenstrom, Jr. |
| 6,045,573 | A | 4/2000 | Wenstrom, Jr. |
| 6,045,574 | A | 4/2000 | Thal |
| 6,056,750 | A | 5/2000 | Lob |
| 6,149,653 | A | 11/2000 | Deslauriers |
| 6,436,124 | B1 | 8/2002 | Anderson |
| 6,527,794 | B1 | 3/2003 | McDevitt |
| 6,551,323 | B2 | 4/2003 | Doubler |
| 6,592,609 | B1 | 7/2003 | Bonutti |
| 6,689,169 | B2 | 2/2004 | Harris |
| 6,723,099 | B1 | 4/2004 | Goshert |
| 7,041,106 | B1 | 5/2006 | Carver |
| D587,807 | S | 3/2009 | Wolf |
| 7,887,551 | B2 | 2/2011 | Bojarski |
| 7,955,388 | B2 | 6/2011 | Jensen |
| 8,070,786 | B2 | 12/2011 | Huebner |
| 8,100,983 | B2 | 1/2012 | Schulte |
| 8,133,261 | B2 | 3/2012 | Fisher |
| 8,511,962 | B2 | 8/2013 | Schuech |
| 8,764,842 | B2 | 7/2014 | Graham |
| 8,834,572 | B2 | 9/2014 | Averous |
| 8,945,193 | B2 | 2/2015 | Kirschman |
| 8,998,999 | B2 | 4/2015 | Lewis |
| 9,044,287 | B2 | 6/2015 | Reed |
| 9,072,562 | B2 | 7/2015 | Weiner |
| 9,072,564 | B2 | 7/2015 | Reed |
| 9,282,977 | B2 | 3/2016 | Penzimer |
| 9,452,002 | B2 | 9/2016 | Roman |
| 9,474,561 | B2 | 10/2016 | Shemwell |
| 9,486,258 | B2 | 11/2016 | Roman |
| 9,538,998 | B2 | 1/2017 | Stone |
| 9,545,274 | B2 | 1/2017 | McCormick |
| 9,554,914 | B2 | 1/2017 | Taylor |
| 9,554,916 | B2 | 1/2017 | Miller |
| 9,642,656 | B2 | 5/2017 | Kotuljac |
| 9,675,392 | B2 | 6/2017 | Shemwell |
| 9,687,256 | B2 | 6/2017 | Granberry |
| 9,717,543 | B2 | 8/2017 | Brown |
| 9,737,294 | B2 | 8/2017 | Wales |
| 9,750,553 | B1 | 9/2017 | Forrester |
| 9,757,168 | B2 | 9/2017 | Seavey |
| 9,833,230 | B2 | 12/2017 | Stone |
| 2001/0037131 | A1 | 11/2001 | Schmieding |
| 2002/0004668 | A1 | 1/2002 | Bartlett |
| 2002/0052629 | A1 | 5/2002 | Morgan |
| 2002/0087190 | A1 | 7/2002 | Benavitz |
| 2002/0120292 | A1 | 8/2002 | Morgan |
| 2002/0120335 | A1 | 8/2002 | Angelucci |
| 2002/0147463 | A1 | 10/2002 | Martinek |
| 2002/0151982 | A1 | 10/2002 | Masini |
| 2002/0161401 | A1 | 10/2002 | Steiner |
| 2003/0004545 | A1 | 1/2003 | Burkhart |
| 2003/0065361 | A1 | 4/2003 | Dreyfuss |
| 2003/0078584 | A1 | 4/2003 | Tipirneni |
| 2003/0083662 | A1 | 5/2003 | Middleton |
| 2003/0144696 | A1 | 7/2003 | Sinnott |
| 2003/0204195 | A1 | 10/2003 | Keane |
| 2004/0030354 | A1 | 2/2004 | Leung |
| 2004/0106950 | A1 | 6/2004 | Grafton |
| 2004/0133239 | A1 | 7/2004 | Singhatat |
| 2004/0193176 | A1 | 9/2004 | Gerngross |
| 2004/0230312 | A1 | 11/2004 | Hanson |
| 2004/0254580 | A1 | 12/2004 | Boock |
| 2005/0038435 | A1 | 2/2005 | Cole |
| 2005/0075668 | A1 | 4/2005 | Lizardi |
| 2005/0080455 | A1 | 4/2005 | Schmieding |
| 2005/0283158 | A1 | 12/2005 | West |
| 2005/0283159 | A1* | 12/2005 | Amara ............... A61B 17/7266 606/75 |
| 2006/0129153 | A1* | 6/2006 | Klaue ................. A61B 17/68 606/916 |
| 2006/0247641 | A1* | 11/2006 | Re ..................... A61B 17/0401 606/232 |
| 2006/0276841 | A1* | 12/2006 | Barbieri ............ A61B 17/0401 606/232 |
| 2007/0005068 | A1* | 1/2007 | Sklar ................ A61B 17/0401 606/139 |
| 2007/0005069 | A1* | 1/2007 | Contiliano ........ A61B 17/0401 606/304 |
| 2007/0032792 | A1* | 2/2007 | Collin ............... A61B 17/0401 606/151 |
| 2007/0112352 | A1* | 5/2007 | Sorensen .......... A61B 17/0401 606/326 |
| 2007/0135841 | A1* | 6/2007 | Dreyfuss ........... A61B 17/0401 606/232 |
| 2007/0142837 | A1* | 6/2007 | Dreyfuss ........... A61B 17/0401 606/232 |
| 2007/0173845 | A1* | 7/2007 | Kim .................. A61B 17/0401 606/232 |
| 2007/0198017 | A1* | 8/2007 | Tschakaloff ....... A61B 17/0401 606/326 |
| 2008/0086139 | A1* | 4/2008 | Bourke ............... A61B 17/68 606/270 |
| 2008/0109038 | A1* | 5/2008 | Steiner .............. A61B 17/0401 606/232 |
| 2008/0125779 | A1* | 5/2008 | Ferree ............... A61B 17/0401 606/246 |
| 2008/0132894 | A1* | 6/2008 | Coilard-Lavirotte ...... A61B 17/1604 606/60 |
| 2008/0147063 | A1* | 6/2008 | Cauldwell ......... A61B 17/0401 606/60 |
| 2008/0177262 | A1* | 7/2008 | Augoyard ............ A61B 17/68 606/70 |
| 2008/0234730 | A1* | 9/2008 | Cotton .............. A61B 17/0401 606/232 |
| 2008/0269743 | A1* | 10/2008 | McNamara ........ A61B 17/0401 606/60 |
| 2008/0306511 | A1* | 12/2008 | Cooper ............. A61B 17/0401 606/232 |
| 2009/0043337 | A1* | 2/2009 | Martin .............. A61B 17/0401 606/232 |
| 2009/0076544 | A1* | 3/2009 | DiMatteo .......... A61B 17/0401 606/232 |
| 2009/0149883 | A1* | 6/2009 | Brunsvold ......... A61B 17/0401 606/232 |
| 2009/0287246 | A1* | 11/2009 | Cauldwell ......... A61B 17/0401 606/232 |
| 2009/0318959 | A1* | 12/2009 | Burkhart .......... A61B 17/0401 606/228 |
| 2010/0016902 | A1* | 1/2010 | Paulk ............... A61B 17/0401 606/300 |

(56) References Cited

U.S. PATENT DOCUMENTS

| | | | |
|---|---|---|---|
| 2010/0049249 A1* | 2/2010 | Lombardo | A61B 17/0401 606/232 |
| 2010/0076503 A1* | 3/2010 | Beyar | A61B 17/1615 606/86 R |
| 2010/0131072 A1* | 5/2010 | Schulte | A61B 17/68 623/21.11 |
| 2010/0222812 A1* | 9/2010 | Stone | A61B 17/0401 606/232 |
| 2010/0262186 A1* | 10/2010 | Sodeika | A61B 17/0401 606/232 |
| 2011/0004255 A1* | 1/2011 | Weiner | A61B 17/1682 606/301 |
| 2011/0054545 A1* | 3/2011 | Champagne | A61B 17/7225 606/301 |
| 2011/0082508 A1* | 4/2011 | Reed | A61B 17/7225 606/329 |
| 2011/0118796 A1 | 5/2011 | Reiley | |
| 2011/0144644 A1* | 6/2011 | Prandi | A61B 17/68 606/62 |
| 2011/0172668 A1 | 7/2011 | Frake | |
| 2011/0208240 A1 | 8/2011 | Stone | |
| 2011/0213426 A1* | 9/2011 | Yedlicka | A61B 17/8635 606/309 |
| 2011/0224727 A1* | 9/2011 | Housman | A61B 17/0401 606/232 |
| 2011/0301648 A1* | 12/2011 | Lofthouse | A61B 17/0401 606/300 |
| 2012/0031792 A1* | 2/2012 | Petit | A61B 17/708 206/438 |
| 2012/0116451 A1* | 5/2012 | Tepic | A61B 17/0401 606/232 |
| 2012/0165864 A1 | 6/2012 | Hernandez | |
| 2012/0197311 A1* | 8/2012 | Kirschman | A61B 17/7064 606/304 |
| 2012/0203340 A1* | 8/2012 | Choinski | A61F 2/0811 623/13.14 |
| 2012/0290003 A1* | 11/2012 | Dreyfuss | A61B 17/0401 606/232 |
| 2013/0023929 A1* | 1/2013 | Sullivan | A61B 17/0401 606/232 |
| 2013/0046351 A1* | 2/2013 | Schwappach | A61F 2/0811 606/323 |
| 2013/0066383 A1 | 3/2013 | Anderson | |
| 2013/0085528 A1* | 4/2013 | DiMatteo | A61B 17/0401 606/232 |
| 2013/0096611 A1* | 4/2013 | Sullivan | A61B 17/0485 606/232 |
| 2013/0103080 A1* | 4/2013 | Hernandez | A61B 17/0401 606/232 |
| 2013/0103081 A1* | 4/2013 | Wolf | A61B 17/0401 606/232 |
| 2013/0123862 A1 | 5/2013 | Anderson | |
| 2013/0131822 A1* | 5/2013 | Lewis | A61F 2/4606 623/21.19 |
| 2013/0150965 A1* | 6/2013 | Taylor | A61F 2/30 623/16.11 |
| 2013/0165972 A1* | 6/2013 | Sullivan | A61B 17/0401 606/232 |
| 2013/0184708 A1* | 7/2013 | Robinson | A61B 17/683 606/60 |
| 2013/0211405 A1* | 8/2013 | Bouduban | A61B 17/7233 606/64 |
| 2013/0245700 A1* | 9/2013 | Choinski | A61B 17/0401 606/300 |
| 2013/0317556 A1* | 11/2013 | Goldzak | A61B 17/7258 606/323 |
| 2013/0325138 A1* | 12/2013 | Graham | A61B 17/68 623/21.15 |
| 2014/0180428 A1* | 6/2014 | McCormick | A61F 2/4225 623/21.19 |
| 2014/0188166 A1* | 7/2014 | Cobb | A61B 17/0401 606/232 |
| 2014/0188179 A1* | 7/2014 | McCormick | A61B 17/7291 606/301 |
| 2014/0188239 A1* | 7/2014 | Cummings | A61B 17/7291 623/21.19 |
| 2014/0214080 A1* | 7/2014 | Wales | A61B 17/7291 606/232 |
| 2015/0142024 A1* | 5/2015 | Arai | A61F 2/0811 606/151 |
| 2015/0150607 A1 | 6/2015 | Chen | |
| 2015/0164563 A1 | 6/2015 | Lewis | |
| 2015/0351815 A1 | 12/2015 | Wales | |
| 2015/0374503 A1 | 12/2015 | Lovick | |
| 2016/0015437 A1 | 1/2016 | Elleby | |
| 2016/0045324 A1 | 2/2016 | Austin | |
| 2016/0287300 A1 | 10/2016 | McCormick | |
| 2017/0000618 A1 | 1/2017 | Tyber | |
| 2017/0007416 A1 | 1/2017 | Sander | |
| 2017/0056078 A1 | 3/2017 | Anderson | |
| 2017/0065424 A1 | 3/2017 | Lauf | |
| 2017/0100172 A1 | 4/2017 | Taylor | |
| 2017/0151061 A1 | 6/2017 | Lavi | |
| 2017/0156877 A1 | 6/2017 | Reed | |
| 2017/0172560 A1* | 6/2017 | Patel | A61B 17/0401 |
| 2017/0189090 A1 | 7/2017 | Champagne | |
| 2017/0224362 A1 | 8/2017 | Hollis | |
| 2017/0252084 A1 | 9/2017 | Anderson | |
| 2017/0319349 A1 | 11/2017 | Kowalczyk | |
| 2017/0333081 A1 | 11/2017 | Cordier | |
| 2017/0340370 A1 | 11/2017 | Chen | |
| 2018/0021145 A1 | 1/2018 | Seavey | |
| 2018/0049881 A1 | 2/2018 | Austin | |
| 2018/0140338 A1 | 5/2018 | Wingenfeld | |

FOREIGN PATENT DOCUMENTS

| | | | |
|---|---|---|---|
| CA | 2146180 | 4/1996 | |
| DE | 29717413 | 3/1999 | |
| EP | 951869 | 10/1999 | |
| FR | 2783699 | 1/2001 | |
| FR | 2840190 | 2/2005 | |
| FR | 2846545 | 9/2005 | |
| FR | 2927529 | 2/2011 | |
| RU | 2458650 | 8/2012 | |
| WO | WO1995017857 | 7/1995 | |
| WO | WO2002009597 | 2/2002 | |
| WO | WO2005063149 | 7/2005 | |
| WO | WO2006081483 | 8/2006 | |
| WO | WO2007114769 | 10/2007 | |
| WO | WO2010062379 | 6/2010 | |
| WO | WO2012056384 | 5/2012 | |
| WO | WO 2012056384 A2 * | 5/2012 | A61F 2/0805 |
| WO | WO2016044053 | 3/2016 | |

* cited by examiner

BONE FIXATION IMPLANT AND MEANS OF FIXATION

BACKGROUND OF THE INVENTION

Field of the Invention

The present invention is in the technical field of bone fixation or arthrodesis or deformity correction. The invention relates to a fixation system for bones of all types utilizing an implant that is placed within all or part of a bony structure. Such systems are used in osteosynthesis, wherein the implant bridges a fracture or joint to provide rigidity and aid in healing of the fracture or fusion site. The implant devices of the present invention may be placed in an intramedullary canal or within a bone either completely or partially. The implant may primarily be used for fixation or for aiding in creating a fusion across more than one bone or within a single bone or bone segment. The implant may be constructed of a biologic material, a synthetic material, and or a resorbable material which may be biologic or synthetic. The implant may have material properties or other means for promoting bone growth (osteoinductive) and or for providing a structure for promoting bone growth (osteoconductive). The implant may be provided in a sterile kit and may be preassembled to an instrument for means of insertion. In addition, the present invention provides resistance to pull-out and or rotation and/or pistoning once implanted. Furthermore, the implant includes a means for attaching a suture for additional tissue fixation. The implant may be indicated for the various bones of the entire skeleton. A "fixation device" or the implant may include any of a variety of devices that secure an object to a bone, including but not limited to staples, bone plates, modular staples, bone screws, pins, blades, suture anchors, and the like.

SUMMARY OF THE INVENTION

The present invention includes an implant or other bone fastening device. The implant may be placed fully or partially within a bone's intramedullary canal or within the bone itself. The implant is used for fixation or for aiding in the creating a fusion across more than one bone or within a single bone or bone segment. The implant may be constructed from a number of biocompatible materials including but not limited to a biologic material, a synthetic material, and or a resorbable material which may be biologic or synthetic. The implant may have material properties or other means for promoting bone growth (osteoinductive) and or for providing a structure for bone growth (osteoconductive). The implant may be provided in a sterile kit and may be preassembled to an instrument for means of insertion. The implant of the present invention can be inserted in an axial direction by simply pushing it into the bone. It does not have to be screwed in. It may optionally be rotated when it is pushed in, but rotation usually is not necessary. In addition, the implant devices of the present invention provide resistance to pull-out and or rotation and or pistoning once implanted. Furthermore, the implant includes a means for attaching a suture for additional tissue fixation.

The devices of the present invention may be of one piece construction or of more than one piece. The embodiments described herein are of one piece construction but it will be apparent to those skilled in the art how to make them from more than one piece based upon the disclosures herein. The preferred embodiment may have a tapered geometry for better purchase in the bone in order to resist pull-out and may provide tissue fixation. The implant also has features for engaging bone in a manner to resist pull-out and or rotation and or pistoning. The present invention has a means for attaching a suture that may be utilized for soft or hard tissue attachment.

The terms "implant", "implant device", "fixation device" and "device" are used interchangeably herein to refer to the devices of the present invention.

DETAILED DESCRIPTION OF THE INVENTION

The present invention includes an implant for spanning and or fixating at least two bone segments of different bones or the same bone. Exemplary embodiments of the current invention are discussed in the figures below. The implant may have bone engaging features and fixation features which are used for tissue attachment. The fixation features provide a means for generating compression across the bone segments to further aid in the healing of the bone. The present invention may have an apparatus or instrument for inserting the implant that is pre-assembled or affixed to the implant. The embodiments described herein may be constructed of any suitable biocompatible material which may be biologic or synthetic. The implant of the current invention may be packaged as an implant kit with the associated instruments needed to complete the implantation.

Figure 1:
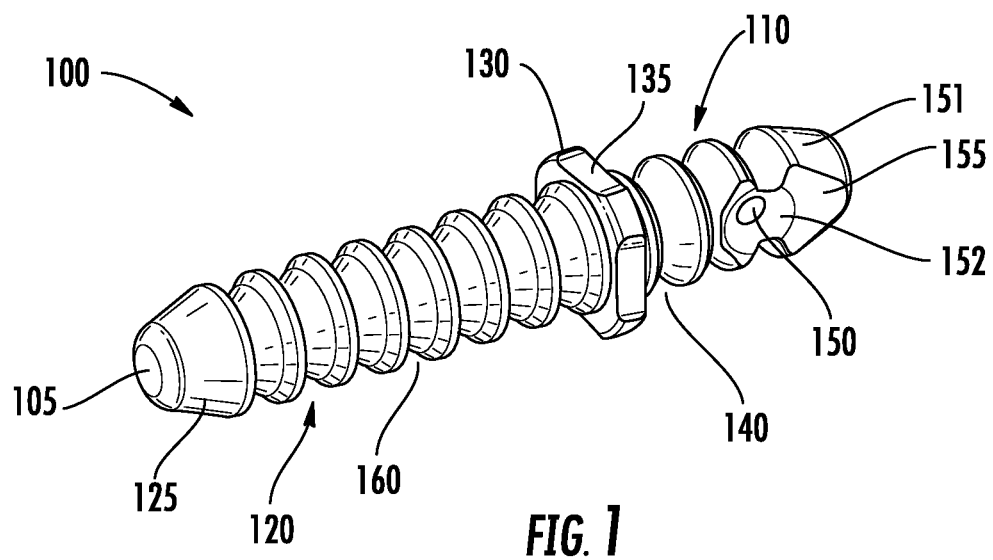
FIG. 1 is a perspective view of a first embodiment of the invention.

FIG. 1 is a perspective view of an implant 100 having a first end 110 and a second end 120. First end 110 may be placed into a first bone segment and second end 120 may be placed into a second bone segment or second end 120 may be placed into a first bone segment and first end 110 may be placed into a second bone segment. The bone segments may be adjacent, opposing bones or the same bone across a fracture or osteotomy site. First end 110 has features 140 that may be rings or barbs for engaging bone. The number of bone engaging features may vary by implant size and geometry. The style of the bone engaging features 140 may also vary to include barbs of various styles, threads, rings, bumps, teeth or the like. The bone engaging features 140 may or may not be circular in cross-section. First end 110 also includes a through hole 150 that may be used with a suture or the like for tissue fixation. The suture and through hole 150 may be used to generate compression between the bone segments that are engaged with implant ends 110 and 120. The compression may be generated by having the second end 120 engaged in bone, while the bone in which first end 110 may be engaged is pulled towards the second end 120 by passing the suture through the hole 150 then through the bone attached to the first end 110 and tightening the suture such that the bones segments are brought together. In this figure, the implant 100 may also act as a tissue anchor and as an aid in fusing or compressing the two bone segments. The use of the suture with through hole 150 also provides a means for resisting rotation and or pistoning of the implant relative to the bone. An alternate embodiment may have the suture pre-assembled to the implant either temporarily or permanently. The suture may or may not be packaged with the implant, pre-threaded through the suture hole, tied to the suture hole, and or injection molded into the implant. The suture may be integral with the implant which may eliminate the through hole 150, but still provide a means for anchoring, generating compression or controlling orientation as described herein. End 110 may also have a surface 155 that may be relatively flat for resisting rotation of the implant 100 in the bone. Hole 150 may have a feature 152 at the transition of the hole 150 to the surface 155 that may prevent tearing or breaking of the suture. End 110 may have a surface 151 that may be tapered for facilitating insertion into the bone. Surface 151 may also be of geometry to prevent stress risers in the bone at the end of the implant. The implant 100 has an end 120 for engaging a bone or segment of bone. As illustrated, end 120 has bone engaging features 160 that may be rings or barbs for engaging bone. The number of bone engaging features 160 may vary by implant size and geometry. The style of the bone engaging features 160 may also vary to include barbs of various styles, threads, rings, bumps, teeth or the like. The bone engaging features 160 may or may not be circular in cross-section. The bone engaging features 160 may or may not be similar to the bone engaging features 140. The type of bone engaging feature may also vary within the same implant. For example bone engaging features 160 may alternate between circular barbs and non-circular rings. End 120 may have surface 125 that may be tapered for facilitating insertion into the bone. Surface 125 may also be of geometry to prevent stress risers in the bone at the end 120. Implant 100 has a cannulation 105 that may extend through the entire length of the implant 100. First end 110 and second end 120 may have feature 130 interposed between them. Feature 130 may serve as a stop to prevent first end 110 or second end 120 from extending too far into a bone segment. Feature 130 may have faces 135 that create a non-circular cross-section and minimize the amount of implant material that may be between two opposing bone segments.

Figure 2:
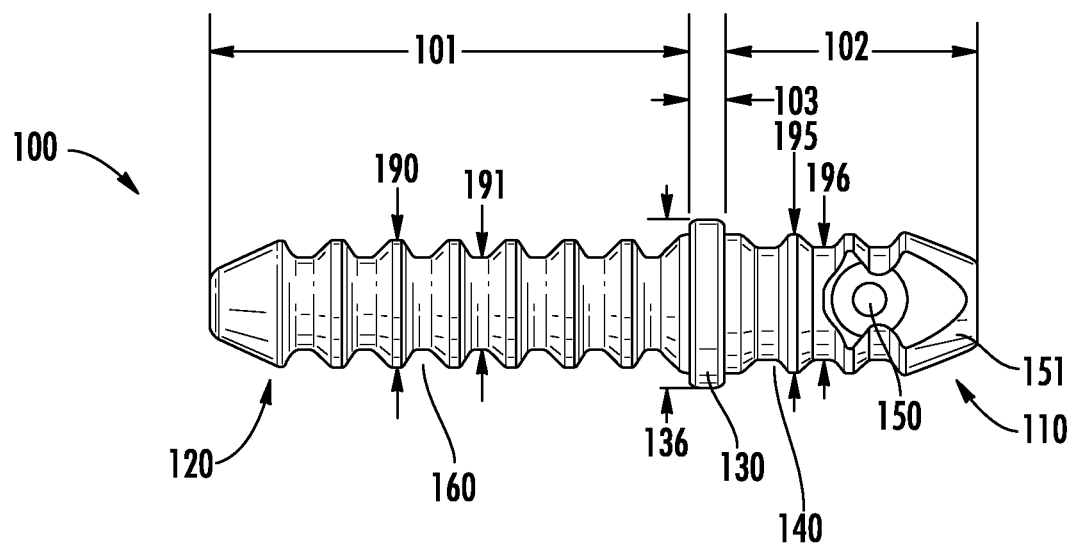
FIG. 2 is a side view of a first embodiment of the invention.

FIG. 2 is a side view of the embodiment of FIG. 1. The first end 110 of the implant 100 has bone engaging features with a major diameter of 195 and a minor diameter of 196. In this figure, the bone engaging features 140 are of uniform size. Other embodiments are possible that may have bone engaging features that are of varying sizes and configurations. The first end 110 may be further defined as having a length 102. Through hole 150 may pass through surface 155 and may extend through certain bone engaging features 140. Through hole 150 may be configured at any location or angle to the long axis of the implant 100. Furthermore, through hole 150 is intended to allow passage of a secondary element (i.e., a suture or insertion instrument) both into and out of the implant 100. Through hole 150 is shown passing from one side of the implant 100 and out of the opposite side, an alternate embodiment may have a passage hole that enters and exits on the same side of the implant 100. Still another embodiment may have a passage hole or suture that enters and exists from the top to bottom of the implant 100. Second end 120 of the implant 100 has bone engaging features with a major diameter of 190 and a minor diameter of 191. In this figure, the bone engaging features 160 are of uniform size. Other embodiments are possible that may have bone engaging features that are of varying sizes and configurations. The second end 120 may be further defined as having a length 101. In this figure, second end 120 is shown not having a through hole 150. (See also FIG. 21 which has through holes 403 and 404.) In an alternate embodiment, second end 120 may have a through hole 150 that may be used with the suture or the like for tissue fixation. The suture and through hole 150 may be used to generate compression between the bone segments that are engaged with the implant ends 110 and 120. The compression may be generated by having the first end 110 engaged in bone, while the bone in which second end 120 may be engaged is pulled towards the first end 110 by passing the suture through the hole 150 then through the bone attached to the second end 120 and tightening the suture such that the bone segments are brought together. In this figure, the implant 100 may also act as a tissue anchor and as an aid in fusing or compressing the two bone segments. In yet other embodiments, both ends 110 and 120 may have through holes 150. Yet further, alternate embodiments may have the suture pre-assembled to the both ends of the implant either temporarily or permanently. The suture may be simply packaged with or without the implant, pre-threaded through the suture holes, tied to the suture hole, and or injection molded into the implant. The suture may be integral with the implant in multiple locations or positions which may eliminate the through holes 150, but still provide multiple means for anchoring, generating compression or controlling orientation as described herein. FIG. 2 shows feature 130 having an effective diameter 136 and a length 103. Some embodiments may require feature 130 to be as small as possible so as not to reduce the bone to bone apposition between the two bone segments.

Figure 3:
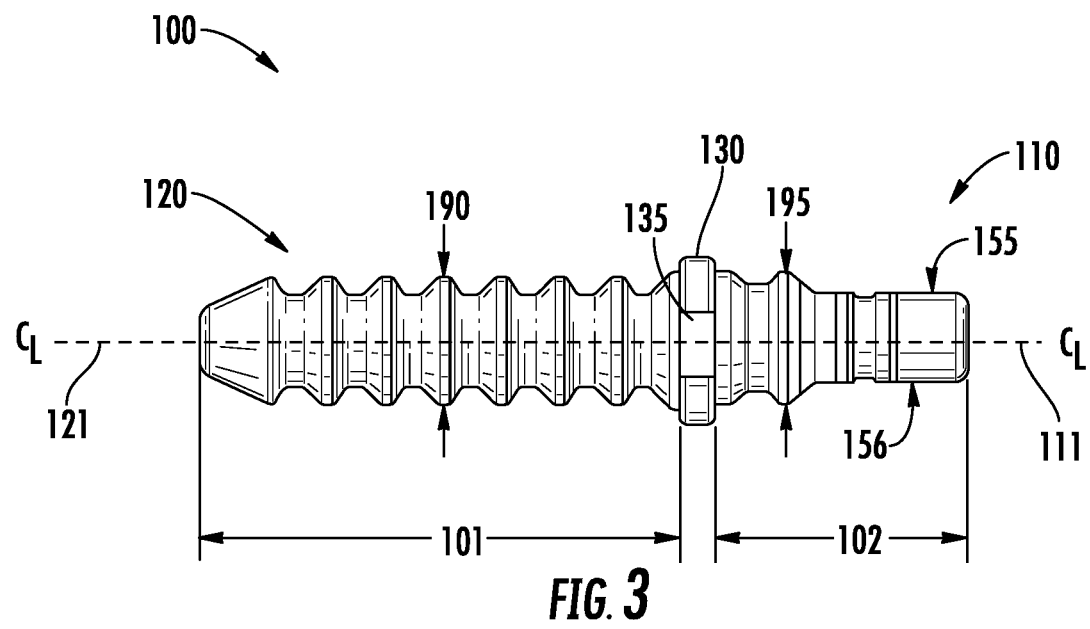
FIG. 3 is a top view of a first embodiment of the invention.

FIG. 3 is a top view of the embodiment described in FIGS. 1 and 2. This figure shows first end 110 having two flats 155 and 156 that may be present. These flats 155 and 156 are used to resist rotation of the implant 100 relative to bone. FIG. 3 shows first end 110 and second end 120 both having a circular cross-section. Alternate embodiments may have a combination of a circular and non-circular ends where first end 110 may be non-circular and second end 120 may be circular or visa versa. The implant is depicted has having a first end 110 and a second end 120 with different lengths 101 and 102. Alternate embodiments may have length 101 and 102 that may or may not be of equal length. The implant is depicted as having a first end 110 and a second end 120 with similar effective outer diameters 190 and 195. Alternate embodiments may have effective outer diameters or dimensions 190 and 195 that may or may not be of equal value. The implant is depicted as having a first end 110 with a centerline 111 and a second end 120 with a collinear centerline 121. Alternate embodiments may have first end 110 with a centerline 111 and second end 120 with a centerline 121 that may or may not be collinear and or parallel.

Figure 4:
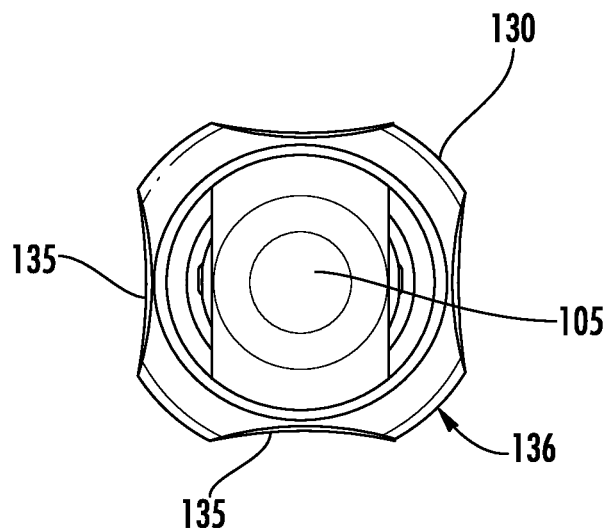
FIG. 4 is an end view of a first embodiment of the invention.

FIG. 4 is an end view of implant 100 that has a cannulation 105 that may extend the entire length of the implant 100. FIG. 4 shows feature 130 having a non-circular cross-section. In an alternate embodiment, feature 130 may or may not have a circular cross-section. The cannulation may be used to facilitate implantation or may be used to accommodate another means of additional fixation.

Figure 5:
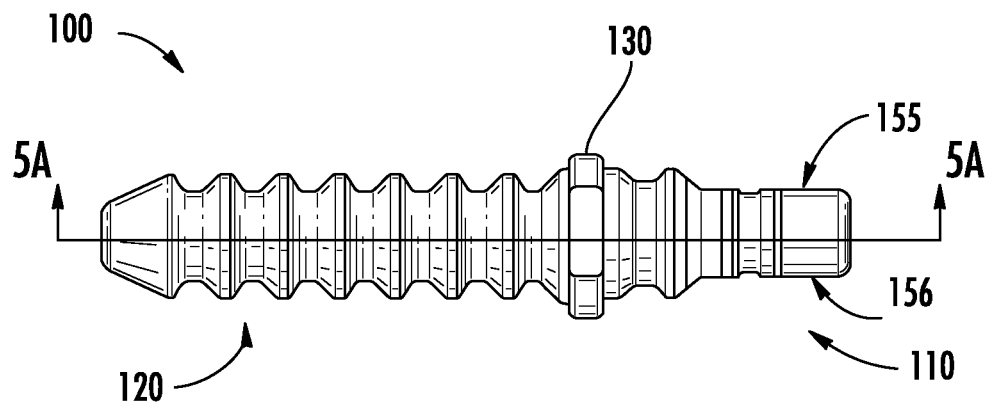
FIG. 5 is a top view of a first embodiment of the invention.
Figure 5A:
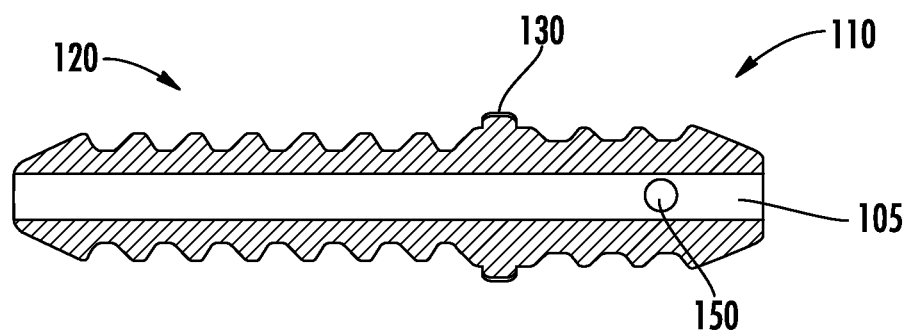
FIG. 5A is the section view A-A of FIG. 5.

FIG. 5 is a side view of implant 100 and FIG. 5A is a section view A-A of the implant 100. The section view A-A shows the cannulation 105 extending through the length of the implant 100. It further shows the through hole 150 intersecting the cannulation and in this embodiment the through hole 150 may extend through the entire width of the implant. Alternate embodiments may or may not include the cannulation 105.

Figure 6:
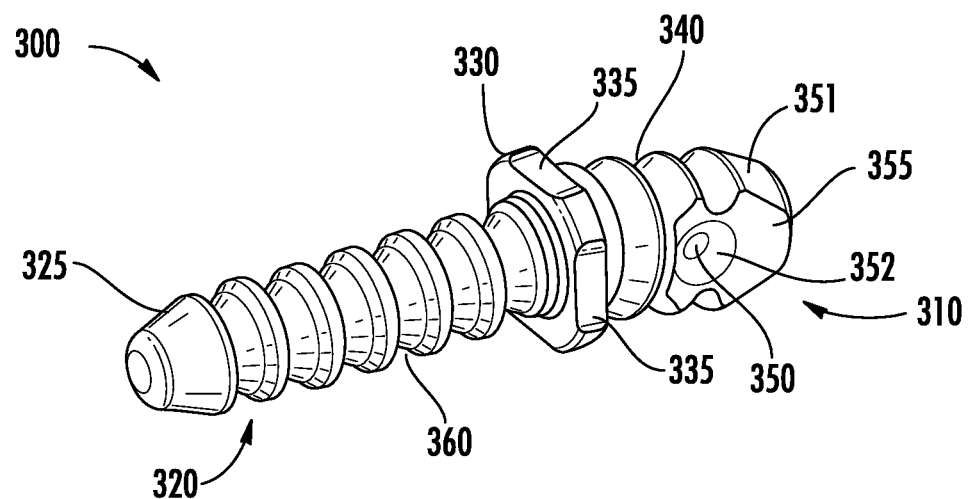
FIG. 6 is a perspective view of a second embodiment of the invention.

FIG. 6 is a perspective view of implant 300, a second embodiment of the invention. Implant 300 has a first end 310 and a second end 320. First end 310 may be placed into a first bone segment and second end 320 may be placed into a second bone segment. The bone segments may be opposing bones or the same bone across a fracture or osteotomy site. First end 310 has features 340 that may be rings or barbs for engaging bone. The number of bone engaging features may vary by implant size and geometry. The style of the bone engaging features 340 may also vary to include barbs of various styles, threads, rings, bumps, teeth or the like. The bone engaging features 340 may or may not be circular in cross-section. First end 310 may also include a through hole 350 that may be used with a suture or the like for tissue fixation or for insertion of the implant into a surgical site. The suture and through hole 350 may be used to generate compression between the bone segments that are engaged with implant ends 310 and 320. The compression may be generated by having the second end 320 engaged in bone, while the bone in which first end 310 is engaged is pulled towards the second end 320 by passing the suture through the hole 350 then through the bone attached to the first end 310 and tightening the suture such that the bones segments are brought together. In this embodiment, the implant 300 may also act as a tissue anchor and as an aid in compressing or fusing the two bone segments. The use of the suture with through hole 350 may also provide a means for resisting rotation and or pistoning of the implant relative to the bone. An alternate embodiment may have the suture pre-assembled to the implant either temporarily or permanently. The suture may be simply packaged with or without the implant, pre-threaded through the suture hole, tied to the suture hole, and or injection molded into the implant. The suture may be integral with the implant, as shown in FIGS. 17a, 17b, 18a, and 18b, which may eliminate the through hole 350, but still provide a means for anchoring, generating compression or controlling orientation as described herein. End 310 may also have a surface 355 that may be relatively flat for resisting rotation of the implant 300 in the bone. Hole 350 may have a feature(s) 352 at the transition of the hole 350 to the surface 355 that may prevent tearing or breaking of the suture. End 310 may have a surface 351 that may be tapered for facilitating insertion into the bone. Surface 351 may also be of a geometry to prevent stress risers in the bone at the end of the implant. Implant 300 may have an end 320 for engaging a bone or segment of bone. End 320 may have bone engaging features 360 that may be rings or barbs for engaging bone. The number of bone engaging features 360 may vary by implant size and geometry. The style of the bone engaging features 360 may also vary to include barbs of various styles, threads, rings, bumps, teeth or the like. The bone engaging features 360 may or may not be circular in cross-section. The bone engaging features 360 may or may not be similar to the bone engaging features 340. The type of bone engaging feature may also vary within the same implant. For example bone engaging features 360 may alternate between circular barbs and non-circular rings. End 320 may have surface 325 that may be tapered for facilitating insertion into the bone. Surface 325 may also be of geometry to prevent stress risers in the bone at the end of the implant. Implant 300 may be solid without the previously described cannulation 105. First end 310 and second end 320 may have feature 330 interposed between them. Feature 330 may serve as a stop to prevent first end 310 or second end 320 from extending too far into a bone segment. Feature 330 may have faces 335 that create a non-circular cross-section and minimize the amount of implant material that may be between two opposing bone segments.

Figure 7:
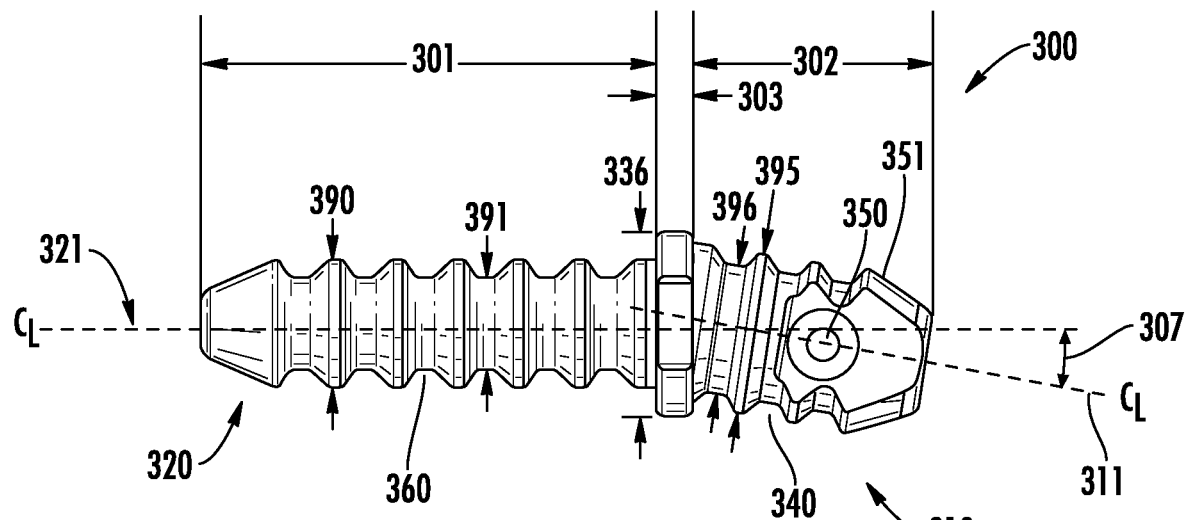
FIG. 7 is a side view of a second embodiment of the invention.

FIG. 7 is a side view of the embodiment of FIG. 6. The first end 310 of implant 300 is shown to have an angle 307 relative to second end 320. The angle 307 may be useful in facilitating deformity correction or may help better correct the normal anatomy. In this figure, angle 307 is shown in one plane. Other embodiments may have more complex or compound angles. The first end 310 of the implant 300 may have bone engaging features with a major diameter of 395 and a minor diameter of 396. This figure further shows the bone engaging features 340 are of uniform size. Other embodiments are possible that may have bone engaging features that are of varying sizes and configurations. The first end 310 may be further defined as having a length 302. Through hole 350 may pass through surface 355 and may extend through certain bone engaging features 340. Second end 320 of the implant 300 may have bone engaging features with a major diameter of 390 and a minor diameter of 391. In this figure, the bone engaging features 360 are of uniform size. Other embodiments are possible that may have bone engaging features that are of varying sizes and configurations. The second end 320 may be further defined as having a length 301. In this figure, second end 320 is shown not having a through hole 350. In an alternate embodiment, second end 320 may have a through hole 350 that may be used with the suture or the like for tissue fixation. The suture and through hole 350 may be used to generate compression between the bone segments that are engaged with the implant ends 310 and 320. The compression may be generated by having the first end 310 engaged in bone, while the bone in which second end 320 may be engaged is pulled towards the first end 310 by passing the suture through the hole 350 then through the bone attached to the second end 320 and tightening the suture such that the bones segments are brought together. This figure further shows that the implant 300 may also act as a tissue anchor and as an aid in compressing or fusing the two bone segments. In yet other embodiments both ends 310 and 320 may have through holes 350. Yet further, alternate embodiments may have the suture pre-assembled to both ends of the implant either temporarily or permanently. The suture may be simply packaged with the implant, pre-threaded through the suture holes, tied to the suture hole, and or injection molded into the implant. The suture may be integral with the implant in multiple locations or positions which may eliminate the through holes 150, but still provide multiple means for anchoring, generating compression or controlling orientation as described herein. FIG. 7 shows feature 330 having an effective diameter 336 and a length 303. Some embodiments may require feature 330 to be as small as possible so as not to reduce the bone to bone apposition between the two bone segments.

Figure 8:
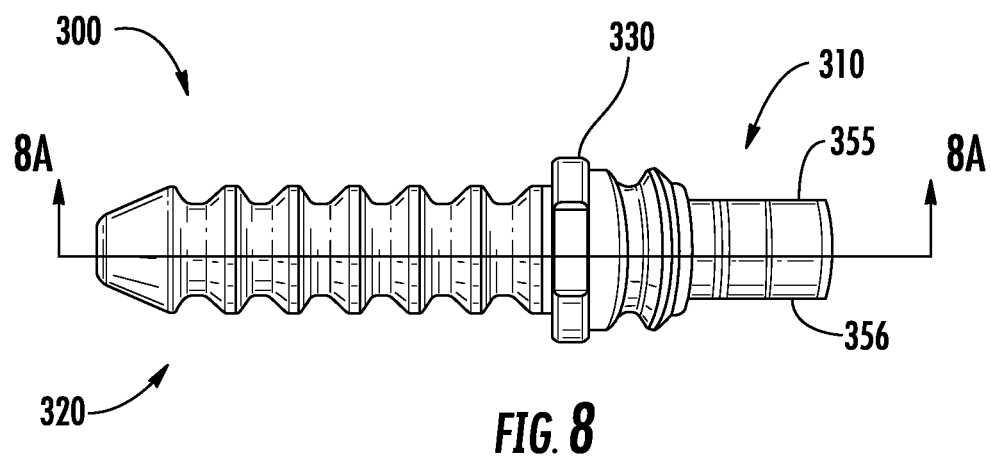
FIG. 8 is a top view of a second embodiment of the invention.
Figure 8A:
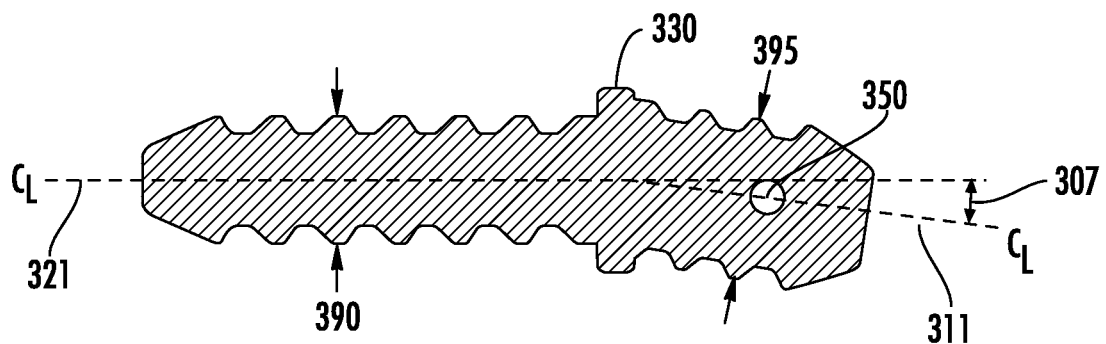
FIG. 8A is the section view A-A of FIG. 8.

FIG. 8 is a top view of the embodiment described in FIGS. 6 & 7. This figure shows first end 310 having two flats 355 and 356 that may be present. These flats 355 and 356 may be used to resist rotation of the implant 300 relative to bone. FIG. 8 shows first end 310 and second end 320 both having a circular cross-section. Alternate embodiments may have a combination of a circular and non-circular ends where first end 310 may be non-circular and second end 320 may be circular or visa versa. The implant is depicted as having a first end 310 and a second end 320 with different lengths 301 and 302. Alternate embodiments may have length 301 and 302 that may or may not be of equal length. The implant is depicted has having a first end 310 and a second end 320 with different effective outer diameters 390 and 395. In this figure, first end 310 has a larger effective diameter 395 than the effective diameter 390 of second end 320. An alternate embodiment may have first end 310 with a smaller effective diameter 395 than the effective diameter 390 of second end 320. Alternate embodiments may have effective outer diameters or dimensions 390 and 395 that may or may not be of equal value. The implant is depicted has having a first end 310 with a centerline 311 and a second end 320 with a non collinear centerline 321. In this embodiment centerline 311 may have angle 307 relative to centerline 321. Alternate embodiments may have first end 310 with a centerline 311 and second end 320 with a centerline 321 that may or may not be collinear and or parallel in multiple planes. FIG. 8 is a side view of the implant 300 and FIG. 8A is a section view A-A of the implant 300. The section view B-B shows the solid cross-section of the implant 300.

Figure 9:
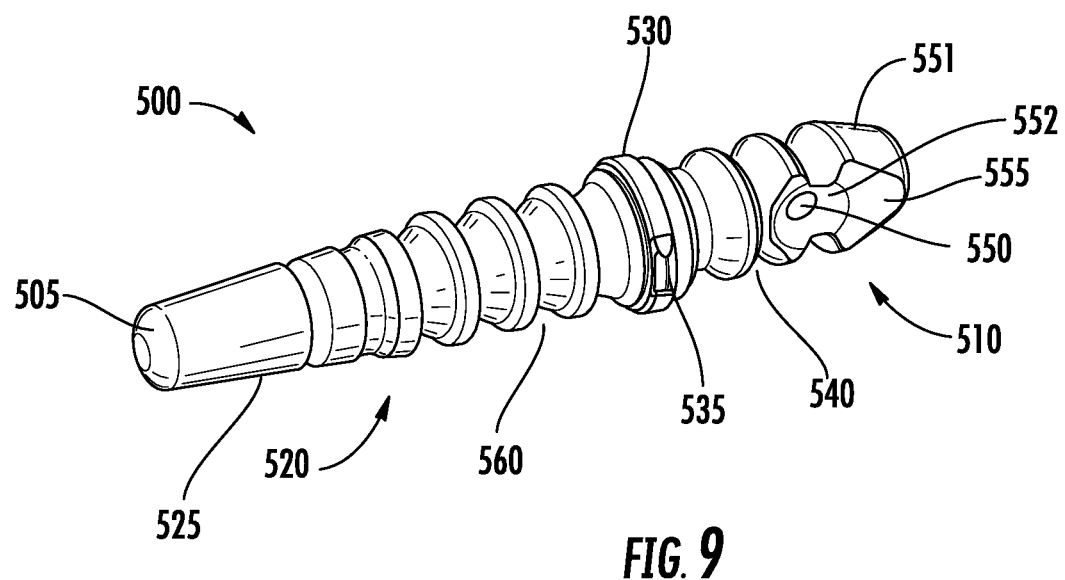
FIG. 9 is a perspective view of a third embodiment of the invention.

FIG. 9 is s a perspective view of implant 500, a third embodiment of the invention. Implant 500 has a first end 510 and a second end 520. First end 510 may be placed into a first bone segment and second end 520 may be placed into a second bone segment. The bone segments may be opposing bones or the same bone across a fracture or osteotomy site. First end 510 has features 540 that may be rings or barbs for engaging bone. The number of bone engaging features may vary by implant size and geometry. The style of the bone engaging features 540 may also vary to include barbs of various styles, threads, rings, bumps, teeth or the like. The bone engaging features 540 may or may not be circular in cross-section. First end 510 may also include a through hole 550 that may be used with a suture or the like for tissue fixation. The suture and through hole 550 may be used to generate compression between the bone segments that are engaged with the implant ends 510 and 520. The compression may be generated by having the second end 520 engaged in bone, while the bone in which first end 510 may be engaged is pulled towards the second end 520 by passing the suture through the hole 550 and then through the bone attached to the first end 510 and then tightening the suture such that the bones segments are brought together. The order/steps of passing the suture through the hole can vary. It can be placed through the implant first then the bone. Or it can be placed through the bone first then the implant. The order of steps isn't critical, as long as the suture passes through the implant. In this figure, the implant 500 may also act as a tissue anchor and as an aid in compressing or fusing the two bone segments. The use of the suture with through hole 550 may also provide a means for resisting rotation and or pistoning of the implant relative to the bone. End 510 may also have a surface 555 that may be relatively flat for resisting rotation of the implant 500 in the bone. Hole 550 may have a feature 552 at the transition of the hole 550 to the surface 555 that may prevent tearing or breaking of the suture. End 510 may have a surface 551 that may be tapered for facilitating insertion into the bone. Surface 551 may also be of a geometry to prevent stress risers in the bone at the end of the implant. Implant 500 may have an end 520 for engaging a bone or segment of bone. End 520 may have bone engaging features 560 that may be rings or barbs for engaging bone. The number of bone engaging features 560 may vary by implant size and geometry. The style of the bone engaging features 560 may also vary to include barbs of various styles, threads, rings, bumps, teeth or the like. The bone engaging features 560 may or may not be circular in cross-section. The bone engaging features 560 may or may not be similar to the bone engaging features 540. The type of bone engaging feature may also vary within the same implant. For example bone engaging features 560 may alternate between circular barbs and non-circular rings. End 520 may have surface 525 that may be tapered. This tapered region 525 may facilitate insertion into the bone and may optimize the engagement with the bone segment. Surface 525 may also be of a geometry to prevent stress risers in the bone at the end of the implant. First end 510 and second end 520 may have feature 530 interposed between them. Feature 530 may serve as a stop to prevent first end 510 or second end 520 from extending too far into a bone segment. Feature 530 may have faces means 535 that create a non-circular cross-section and minimize the amount of implant material that may be between two opposing bone segments. Means 535 may also act as features that key into one or more bone segments. Means 535 may resist rotation of the implant 500 relative to the bone segment(s). Means 535 may also serve to maintain a relative orientation between the implant and bone segments.

Figure 10:
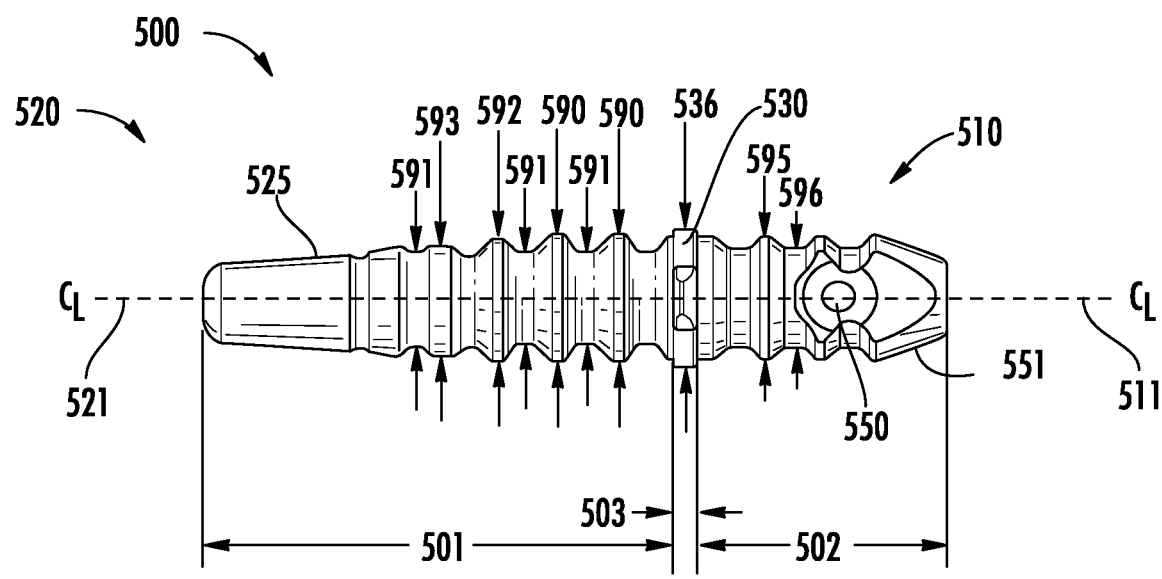
FIG. 10 is a side view of a third embodiment of the invention.

FIG. 10 is a side view of the embodiment of FIG. 9. The first end 510 of the implant 500 may have bone engaging features with a major diameter of 595 and a minor diameter of 596. In this figure, the bone engaging features 540 are of uniform size. Other embodiments are possible that may have bone engaging features that are of varying sizes and configurations. The first end 510 may be further defined as having a length 502. Through hole 550 may pass through surface 555 and may extend through certain bone engaging features 540. Second end 520 of the implant 500 may have bone engaging features with a major diameter of 590 and a minor diameter of 591. In this figure, the bone engaging features 560 vary along the length 501. The minor diameter 591 may be equivalent for bone engaging features 560 while the major or outer diameters 590, 592 and 593 vary in size along the length 501. The varying diameters 590, 592, and 593 may be a result of taper geometry 525. Based on the description herein, those skilled in the art will understand that other embodiments are possible that may have bone engaging features that are of varying sizes and configurations. The second end 520 may be further defined as having a length 501. In this figure, second end 520 is shown not having a through hole 550. In an alternate embodiment, second end 520 may have a through hole 550 that may be used with the suture or the like for tissue fixation or for insertion of the implant into a surgical site. The suture and through hole 550 may be used to generate compression between the bone segments that are engaged with the implant ends 510 and 520. The compression may be generated by having the first end 510 engaged in bone, while the bone in which second end 520 may be engaged is pulled towards the first end 510 by passing the suture through the hole 550 then through the bone attached to the second end 520 and tightening the suture such that the bones segments are brought together. In this figure, the implant 500 may also act as a tissue anchor and as an aid in compressing the two bone segments. In yet other embodiments both ends 510 and 520 may have through holes 550. FIG. 10 is a side view showing feature 530 having an effective diameter 536, a length 503 and a feature 535. Some embodiments may require feature 530 to be as small as possible so as not to reduce the bone to bone apposition between the two bone segments.

Figure 11:
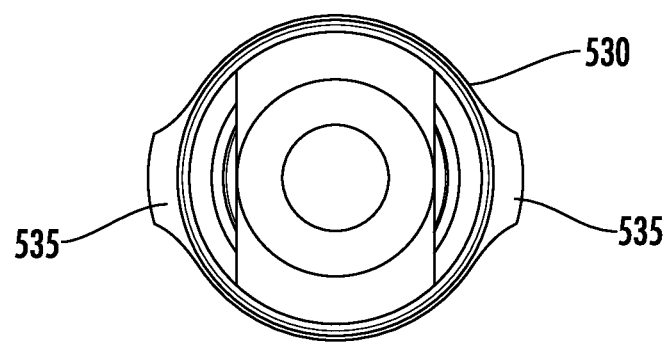
FIG. 11 is an end view of a third embodiment of the invention.

FIG. 11 is an end view of the implant 500. This view shows the feature 530 having a relatively circular cross-section with means 535 that may be equally positioned on opposite sides of the implant 500. Alternate embodiments are possible that may have one or more means 535 that may or may not be equally spaced. In an alternate embodiment, feature 530 may or may not have a circular cross-section.

Figure 12:
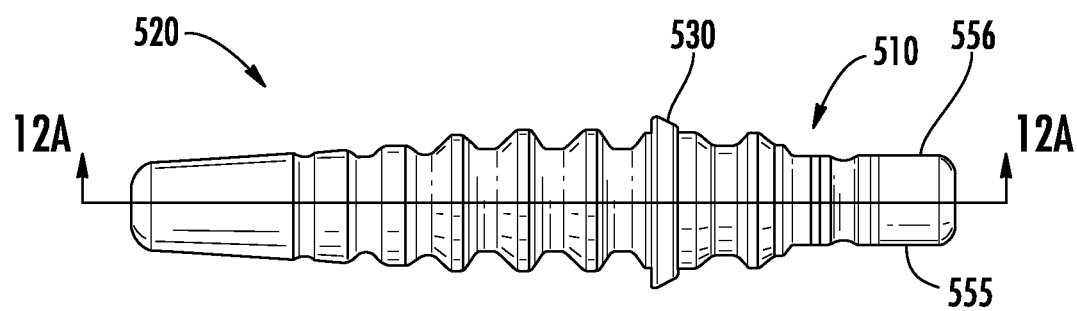
FIG. 12 is a top view of a third embodiment of the invention.
Figure 12A:
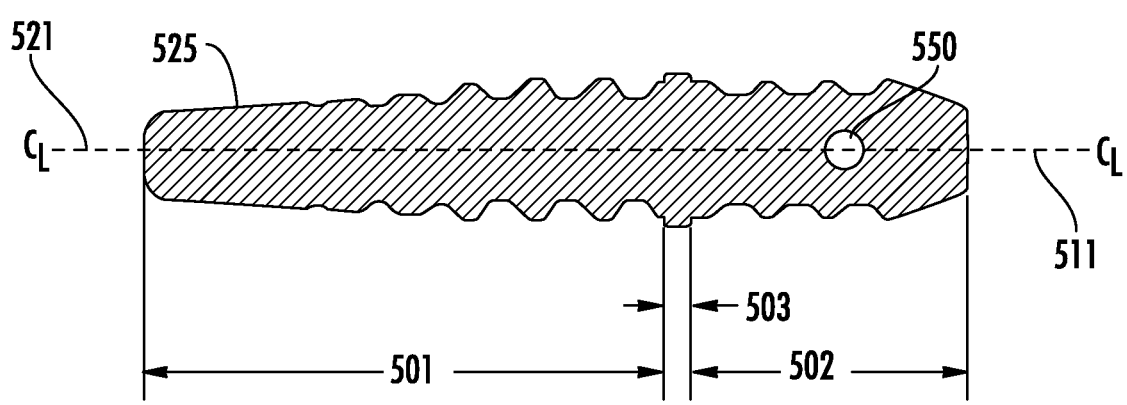
FIG. 12A is the section view A-A of FIG. 12.

FIG. 12 is a top view and a section view of the third embodiment. This figure shows first end 510 having two flats 555 and 556 that may be present. These flats 555 and 556 may be used to resist rotation of the implant 500 relative to bone. FIG. 12 shows first end 510 and second end 520 both having substantially circular cross-sections. Alternate embodiments may have a combination of circular and non-circular ends where first end 510 may be non-circular and second end 520 may be circular or visa versa. The implant is depicted has having a first end 510 and a second end 520 with different lengths 501 and 502. Alternate embodiments may have lengths 501 and 502 that may or may not be of equal length. The implant is depicted has having a first end 510 with a centerline 511 and a second end 520 with a collinear centerline 521. Alternate embodiments may have first end 510 with a centerline 511 and second end 520 with a centerline 521 that may or may not be collinear and or parallel. The section view C-C of FIG. 12 shows the implant 500 with a solid cross-section. It further shows the through hole 550 intersecting the centerline 511 which may also be off centerline.

Based on the description herein, those skilled in the art will understand that multiple variations of implant geometries are possible that are within the scope of the current invention. The descriptions herein discuss embodiments that may or may not include a pre-assembled suture or the like. A pre-assembled suture may be attached to the implant either temporarily or permanently. The suture may or may not be packaged with the implant, pre-threaded through the suture hole, tied to the suture hole or injection molded into the implant. The inclusion or exclusion of the suture for the descriptions herein is not intended to be limiting in scope. The foregoing embodiments and the embodiments described below may be manufactured from a number of materials including titanium, nitinol, stainless steels, PEEK, polymers, biologics, grafts, and/or resorbable materials. The exemplary embodiments described herein are not intended to be limiting.

Figure 13:
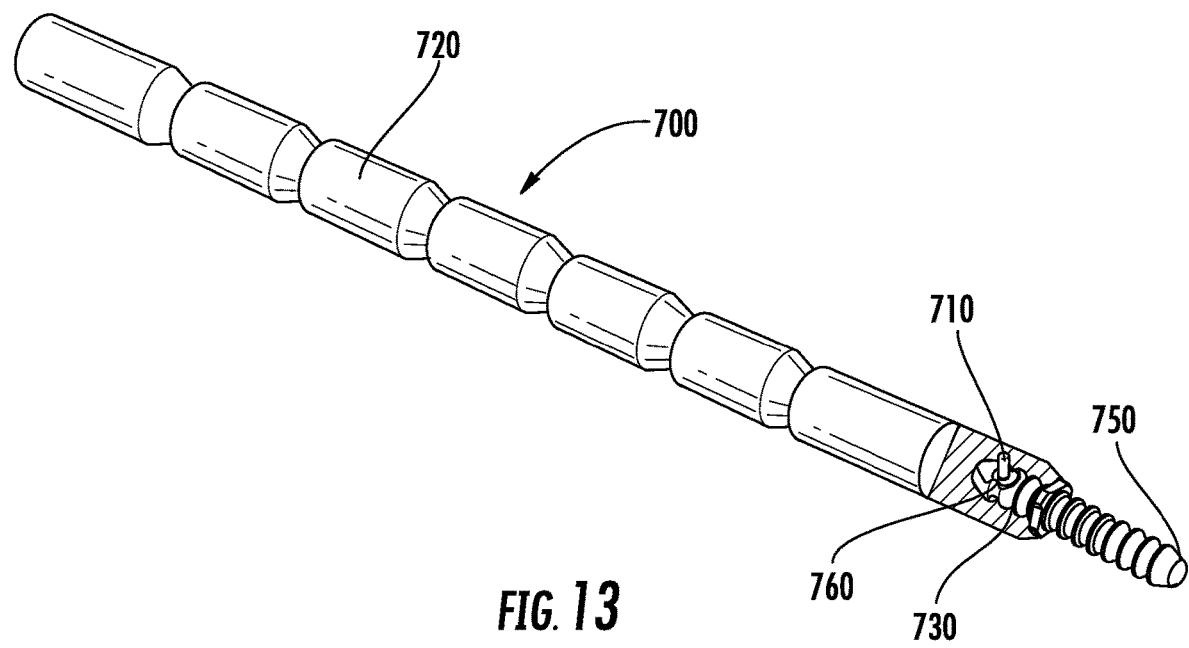
FIG. 13 is a perspective view of on an exemplary embodiment of the invention shown assembled to an insertion device.

FIG. 13 is one possible embodiment of an instrument for means of insertion of an implant of the invention into the surgical site. The instrument for means of insertion, e.g. the inserter 700 may or may not be preassembled to the implant 750. Inserter 700 has a handle region 720 to facilitate insertion and manipulation of the implant during insertion. The inserter 700 may have a connecting end 730 that may be customized for a particular implant embodiment. In this figure, connecting end 730 has a connecting member 710 that engages the through hole 760 of an implant 750. The implant may or may not be preassembled to the inserter.

Figure 14:
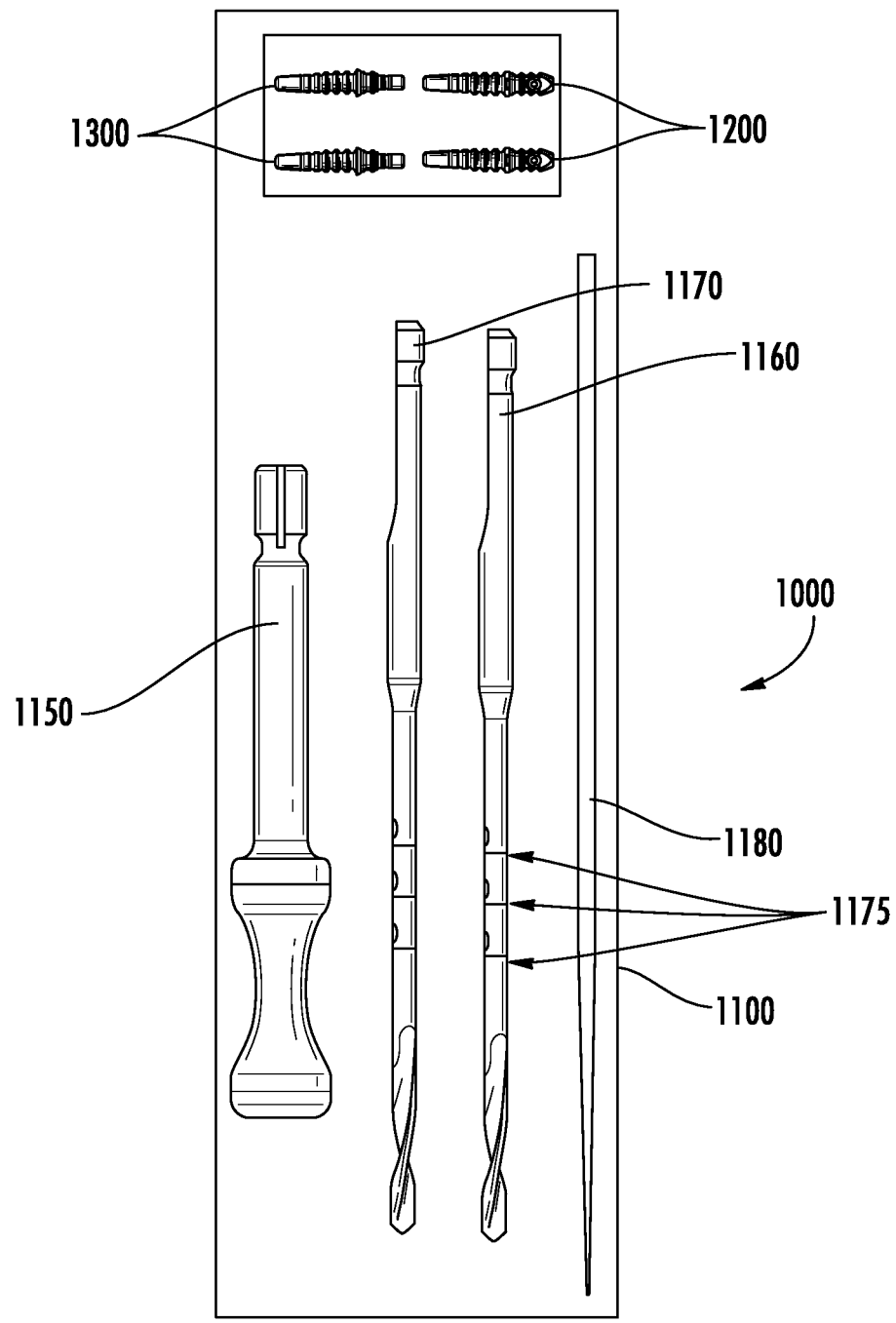
FIG. 14 is a top view of a surgical kit describing the implant and instruments of the invention.

FIG. 14 is one possible embodiment of a kit 1000. Kit 1000 may be provided sterile or non-sterile and may include necessary instruments for completing a surgical procedure. This kit 1000 consists of a tray 1100 that may include an inserter/driver 1150 that may or may not be preassembled to the implant, a first drill/reamer 1160, a second drill/reamer 1170, and a k-wire or a suture passer 1180. This embodiment includes implants 1200 and 1300. The Implants 1200 and 1300 may be included in various sizes or may not be included in the kit. The implants 1200 and 1300 may be provided as individually packaged items or may be included as a component of kit 1000. The drill/reamer 1160 and or 1170 may be included in a number of varying diameters. The reamers 1160 and 1170 may or may not be the same diameter. It may be advantageous for reamers 1160 and 1170 to be different diameters. The kit 1000 may include any number for reamers of the same diameter or different diameters. The size diameter used for drill/reamer 1160 and or 1170 may depend on the tightness of fit between the implant and bone as desired by the end user. The amount of pressfit or tightness of fit between the implant and bone may vary by user and may vary depending on surgeon preference, bone quality, bone geometry, etc. The drill/reamers 1160 and 1170 may include markings or indications 1175 that may be used to provide a reference for appropriate reaming or drilling depth. The reamers/drills 1160 and 1170 may have one or more markings 1175. The markings 1175 may be in multiple locations or configurations. The indications or markings 1175 may provide a visual or physical calibration for indicating depth or some other predetermined measurement. The configuration of the implant kit 1000 is not intended to be limiting. Based on the description herein, those skilled in the art will agree multiple kit configurations may be possible.

The kit 1000 or a similar kit embodiment may be used to prepare a bone for implantation. For exemplary purposes, a possible hammertoe or PIP fusion technique is described. An implant template and the patient's radiographs may be used to approximate the appropriate sized implant to be used. The profile of the implant must fit within the internal boundary of the cortical shell of the phalanges under surgical consideration. The planned amount of bone resection should be taken into account when evaluating implant position and size. Correct implant sizing is critical. The final sizing and fit of the implant must be evaluated with the actual implant to ensure proper fit within the bone. The surgeon should create an appropriate incision over the dorsal aspect of the PIP joint. A transverse capsulotomy with release of the collateral ligaments off the head of the proximal phalanx should be performed. The joint dissection and access should provide complete visualization of the articular surfaces of the middle and proximal phalanges. The appropriate bone cuts should be made perpendicular to the long axis of the phalanges. The final toe orientation is achieved by the angle of the bone resection. If the implant is angled, the bone resection should approximate the angle of the implant. The distal head of the proximal phalanx just posterior to the head of the phalange may be resected. The appropriate sized implant is selected. The appropriately sized reamer may be used to verify implant sizing. The appropriate implant reamer may be sterile packaged with the implant kit. A smaller diameter drill or reamer may be used to create an initial pilot hole if desired. The tip of the reamer may be inserted into the proximal phalanx along its central axis while verifying the correct position of the reamer with dorsal-plantar and medial-lateral fluoroscopy views. After the reamer location has been verified, the reamer may be advanced to the minimum required depth as indicated on the reamer, ensuring no to pierce the proximal cortex of the proximal phalanx. Correct trajectory of the implant is critical. Implants that are misaligned may prevent proper bone apposition and subsequent healing of the fusion site. If the reamer is not fully seated to the indicated mark(s) 1175, the hole may not be drilled to the correct depth. With insufficient reamer depth in the bone, final seating of the implant in the phalanx may be difficult or not possible. The tip of the implant reamer may be inserted into the middle phalanx along its central axis verifying the correct position of the reamer with dorsal-plantar and medial-lateral fluoroscopy views. The implant which may be preloaded onto the instrument for means of insertion, e.g. the inserter, is selected and driven into the proximal phalanx by pushing the implant into the proximal phalanx until the inserter bottoms out on the resected bone surface. Slight tapping may be needed to fully seat the implant in the proximal phalanx then the inserter is removed leaving the middle barbed portion exposed.

If the suture hole is to be used, prior to inserting the distal end of the implant into the middle phalanx, pass the desired suture though the hole in the implant. Prepare a small hole in the proximal dorsal aspect of the middle phalanx. The suture will be passed through this hole. The order/steps of passing the suture through the hole can vary. It can be placed through the implant first then the bone. Or it can be placed through the bone first then the implant. The order of steps isn't critical, as long as the suture passes through the implant. With the suture passed through the implant and the middle phalanx, insert the distal end of the implant into the middle phalanx by positioning inserting the end of the implant into the pre-drilled hole in the middle phalanx. Apply axial force by firmly compressing the joint until the implant is fully seated and the resected surfaces of the proximal and middle proximal phalanges come into contact. With the implant fully seated and the implant positioned and alignment verified, the surgeon may proceed with his preferred closure which may be used to provide additional compression or fixation by tightening the suture such that the bone segments are brought closer together. The final closure and ligament reattachment may be performed with the suture that has been passed through the implant suture hole.

Figure 15:
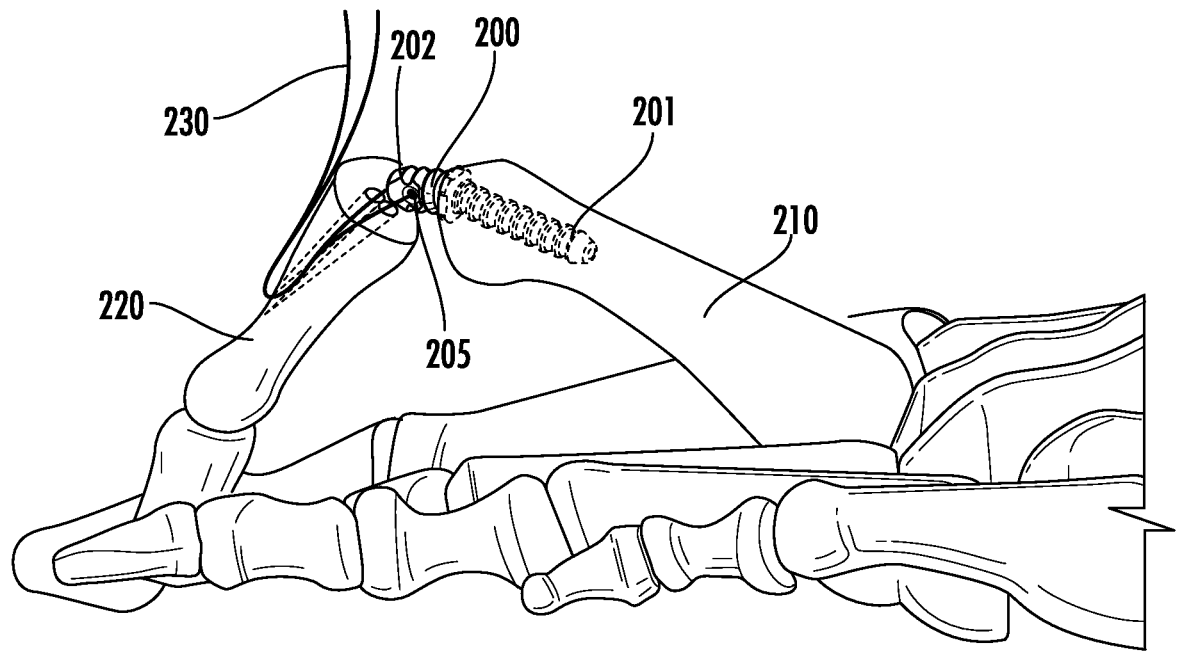
FIG. 15 is a side view of one exemplary embodiment of the invention in one potential application showing the implant not fully inserted into the bone with a suture.
Figure 16:
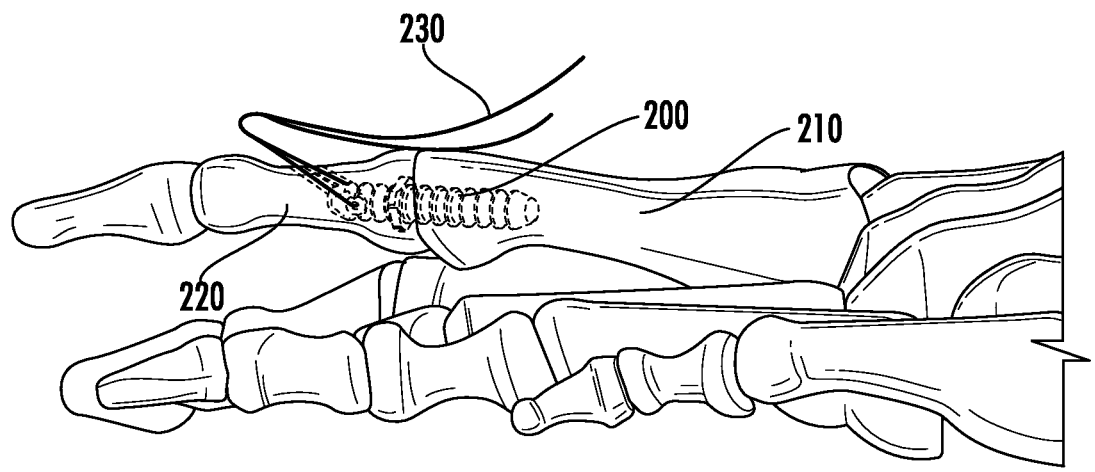
FIG. 16 is a side view of one exemplary embodiment of the invention in one potential application showing the implant in fully inserted into the bone with a suture extending from the implant and the bone for soft tissue attachment.

FIG. 15 is a side view of an implant 200 that may have been inserted into the proximal bone segment 210 with a technique similar to the one described here in. The implant 200 has a first end 201 that may be partially inserted into the bone 210 leaving a second end 202 of the implant 200 exposed. Suture 230 is shown passing through the implant suture hole 205, but prior to full implantation. FIG. 16 is a side view of the implant 200 fully implanted with the suture 230 passing through the suture hole 205 in the second end 202 of the implant 200. The suture 230 may also pass through the second bone 220 for final closure and or tissue attachment. When the suture 230 is securely tightened to bone 220 it may provide additional compression between bones 210 and 220.

Figure 17A:
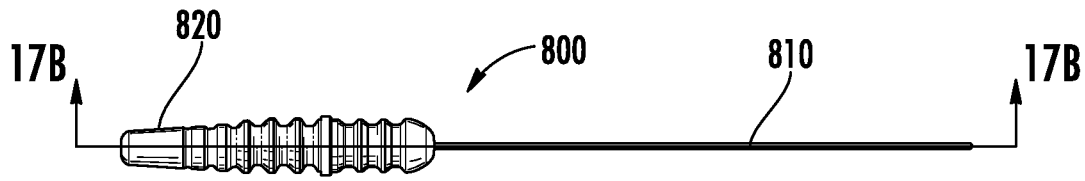
FIG. 17A is the section view of the fourth embodiment shown in FIG. 17.
Figure 17B:
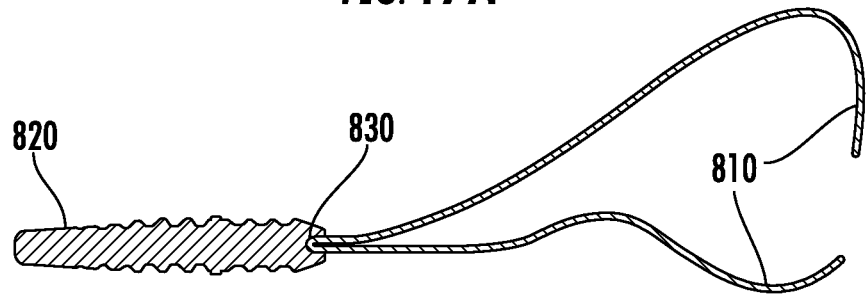
FIG. 17 is a top view of a fourth embodiment of the invention with a section line A-A showing a double suture integral to the implant.

FIG. 17 is a top view of a fourth embodiment of the invention. Implant assembly 800 is illustrated with a section line A-A showing a double suture 810 integral to the implant 820. FIG. 17A is the section view showing the connection area 830 between the implant 820 and double suture 810. The implant 820 may be of any configuration of the current invention described herein. The double suture 810 may be connected or attached to implant 820 at a connection area 830. The double suture 810 may be non resorbable or resorbable. The suture 810 may be of any appropriate size. The attachment 830 may be temporary or the attachment 830 may be permanent. The double suture 810 may be integral to the implant 820. The double suture 810 may be connected or attached to the implant 820 by means of permanently attaching the suture 810 to the implant 820. The attachment 830 may be made by injection molding, insert molding, adhering, tying or other attachment means known to those skilled in the art.

Figure 18A:
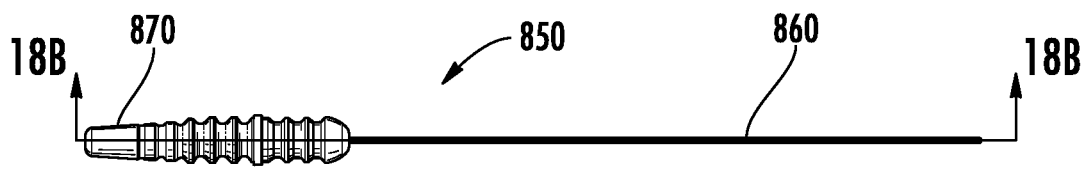
FIG. 18A is the section view of the fifth embodiment shown in FIG. 18.
Figure 18B:
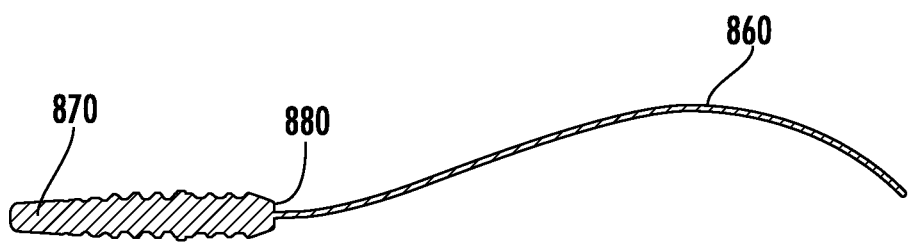
FIG. 18 is a top view of a fifth embodiment of the invention with a section line A-A showing a single suture integral to the implant.

FIG. 18 is a top view of a fifth embodiment of the invention. Implant assembly 850 is illustrated with a section line A-A showing a single suture 860 integral to the implant 870. FIG. 18A is the section view showing the connection area 880 between the implant 870 and suture 860. The implant 870 may be of any configuration of the invention described herein. The suture 860 may be connected or attached to implant 870 at a connection area 880. The suture 860 may be non resorbable or resorbable. The suture 860 may be of any appropriate size. The attachment 880 may be temporary or the attachment 880 may be permanent. The suture 860 may be integral to the implant 870. The suture 860 may be connected or attached to the implant 870 by means of permanently attaching the suture 860 to the implant 870. The attachment 880 may be made by injection molding, insert molding, adhering, tying or other attachment means known to those skilled in the art.

Figure 19:
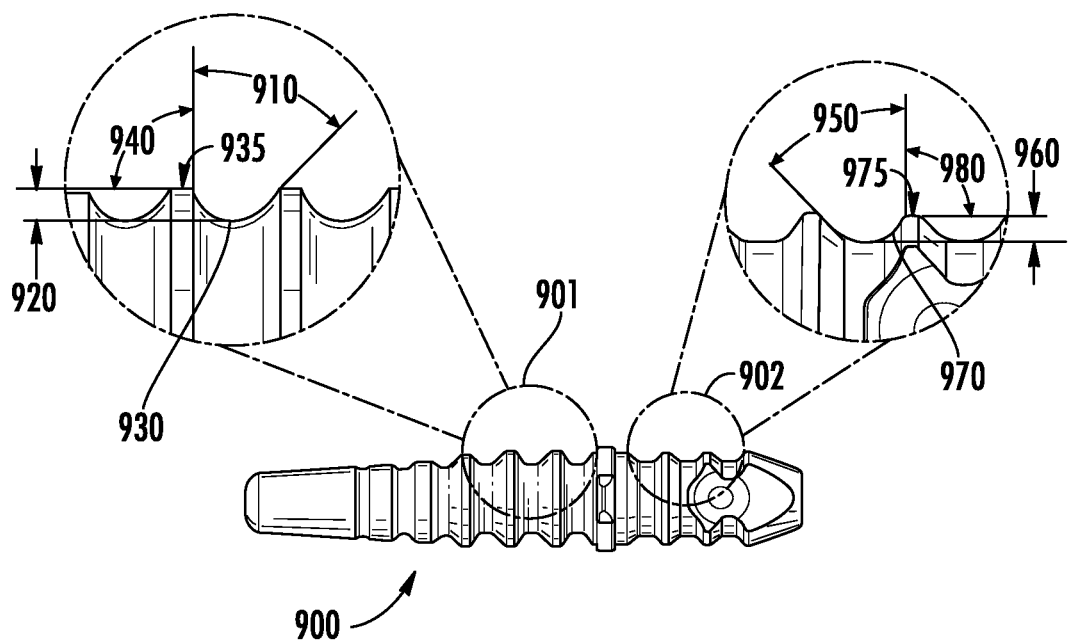
FIG. 19 is a side view showing the detail of an embodiment of the bone engaging features of the invention.

FIG. 19 is a side view showing the detail of one possible embodiment of the bone engaging features of the current invention. The implant 900 has bone engaging features 901 and 902. Bone engaging features 901 and 902 may or may not be of the same geometry. In this embodiment bone engaging features 901 and 902 are mirror images and may allow improved purchase and prevent pullout of the implant 900 when the implant 900 is implanted into opposing bones. Bone engaging feature 901 has an angle 910 with a depth of 920 and a radius of 930. Bone engaging feature 901 has a face 935 that is at an angle 940. Bone engaging feature 902 has an angle 950 with a depth of 960 and a radius of 970. Bone engaging feature 902 has a face 975 that is at an angle 980. Angles 910 and 950 may or may not be of equal value or similar direction but the direction of the angle is critical to the implant locking into the canal of the bone. As shown in FIG. 19, angles 910 and 950 are angled toward the shoulder 530. This orientation creates a sharp corner, angle 940 and 980, that will tend to resistively engage the prepared bone canal when a force is applied in the reverse direction of insertion. This feature advantageously holds the middle and proximal phalanges in direct opposition. Depths 960 and 920 may or may not be of equal value, orientation or geometry. Radii 930 and 970 may or may not be of equal value or orientation. Faces 935 and 975 may or may not be of equal length or similar geometry. Faces 935 and 975 may or may not be collinear.

Figure 20:
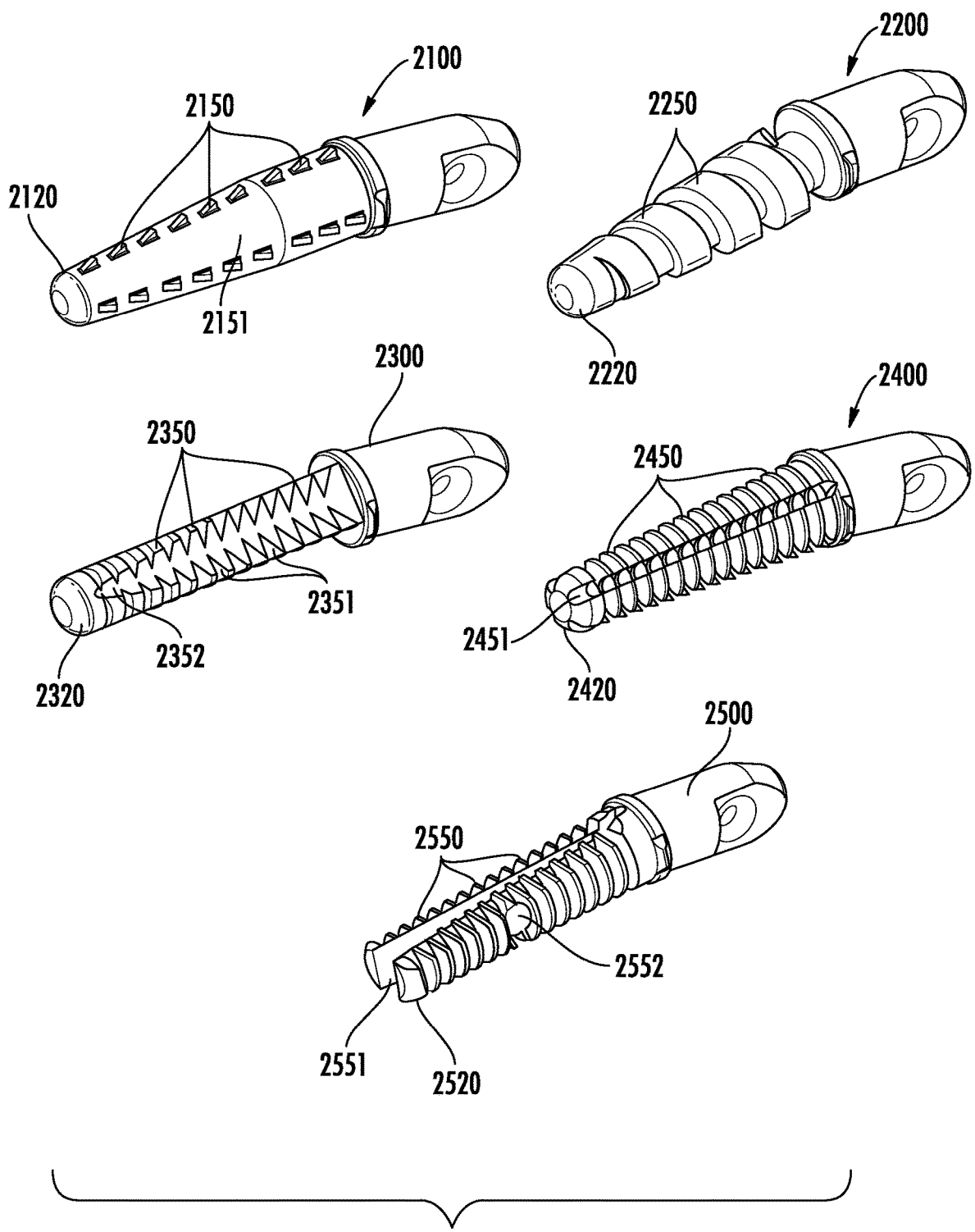
FIG. 20 is a perspective view of multiple possible alternate embodiments of the bone engaging features of the invention.

FIG. 20 is a perspective view of multiple possible alternate embodiments of the bone engaging features of the current invention. Implant 2100 is shown with a first end 2120. First end 2120 may have a plurality of bone engaging features 2150 that are barb like and may be spaced along the length of first end 2120 and around the perimeter of first end 2120. First end 2120 may have areas 2151 that may be void of bone engaging features such as 2150. Implant 2200 has a first end 2220. First end 2220 may have bone engaging features 2250 that may be helical in nature. Implant 2300 has first end 2320. First end 2320 may have bone engaging features 2350. Bone engaging features 2350 may have features 2352 and a geometry that may be used to create features 2351. Bone engaging features 2351 may vary in geometry and sharpness along the length of first end 2320. Implant 2400 may have first end 2420. First end 2420 may have bone engaging features 2450 and groove(s) 2451. Bone engaging features 2450 may vary in size, sharpness and geometry along the length of first end 2420. Implant 2500 may have a first end 2520. First end 2520 may have bone engaging features 2550. Bone engaging features 2550 may be interrupted by hole(s) 2552. Bone engaging features may further be interrupted by slot 2551 that may cause the first end 2520 to expand or be expandable. As will be apparent to those skilled in the art based upon the disclosures herein, an implant of the invention may have one or multiple types of bone engaging features to optimize effectiveness of the implant for its intended purpose.

Figure 21:
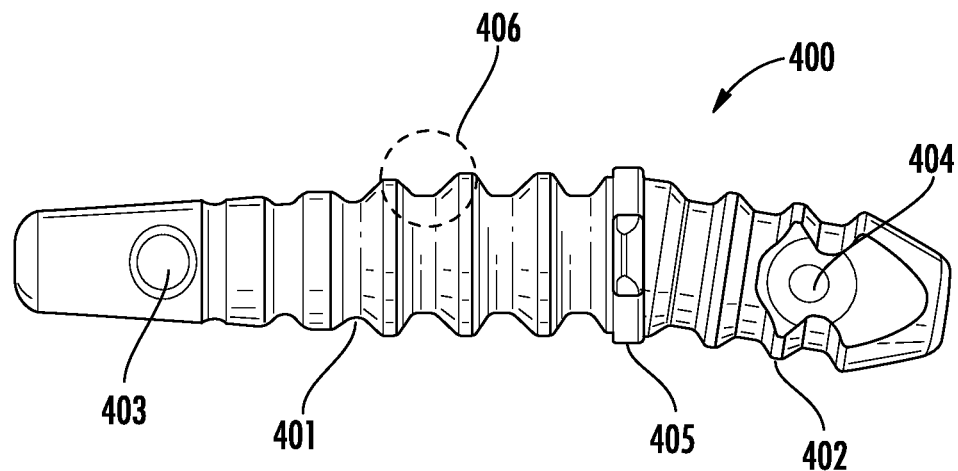
FIG. 21 is a side view of a sixth embodiment depicting a hole in either end of the implant.

FIG. 21 is a side view of an implant 400 similar to the embodiment shown in FIGS. 9 and 10 but in addition to a through hole 404 in the distal end 402, the implant 400 also has a through hole 403 in the proximal end 401. Implant 400 may also include bone engaging features 406 and or a means 405 for determining orientation and or position in a bone.

Figure 22:
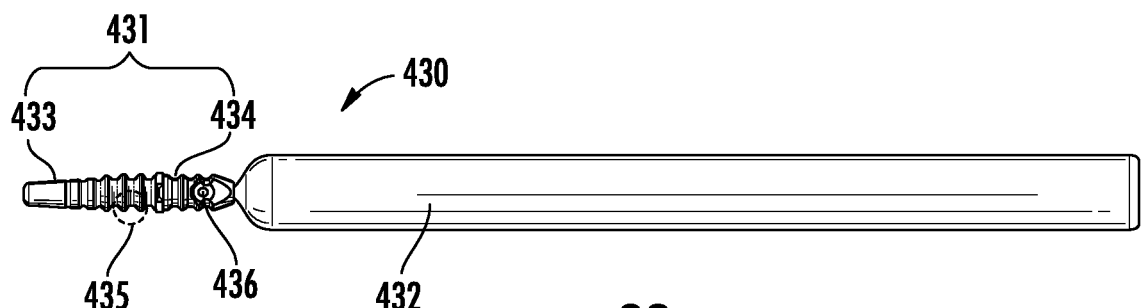
FIG. 22 is a side view of a seventh embodiment depicting an implant releaseably attached to an inserter/driver.
Figure 23:
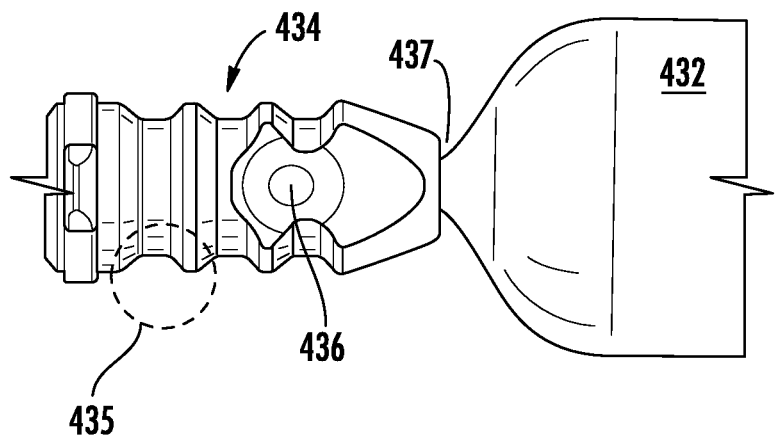
FIG. 23 is a close-up view of the connection means of the embodiment shown in FIG. 22.

FIG. 22 shows a seventh embodiment 430 of the current invention. Device 430 has an implant 431 that is attached to a driver end 432. Implant 431 may be releaseably attached to driver 432 such that after implantation the driver end 432 may be snapped or broken off. The implant 431 has a proximal end 433 and a distal end 434. The implant 431 may have bone engaging features 435 and or a through hole 436 as previously described herein. As depicted in FIG. 23, implant 431 is attached at one end to a driver 432. As shown, the attachment 437 is at the distal end 434 of implant 431 but may also be at the proximal end 433. The attachment 437 will be of a geometry that will allow transfer of sufficient force and manipulation for insertion while allowing the driver end 432 to be removed by either breaking, snapping or cutting the connection attachment means 437. This may be advantageous to allow the implant and inserter to be manufactured from the same material by conventional manufacturing processes such as machining or injection molding. This may reduce the cost of the device and may provide for additional recycling of the driver material. This may be further advantageous in reducing surgical complexity and or surgical time.

Figure 24:
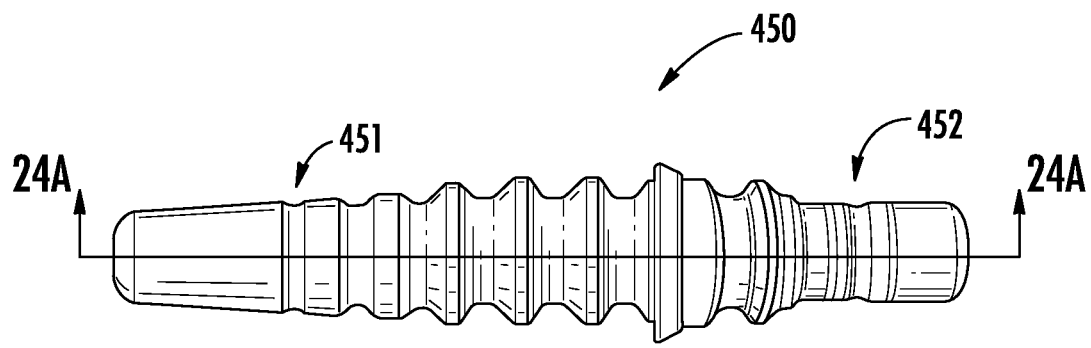
FIG. 24 is a top view of an eighth embodiment depicting a design of the invention with a core member.
Figure 24A:
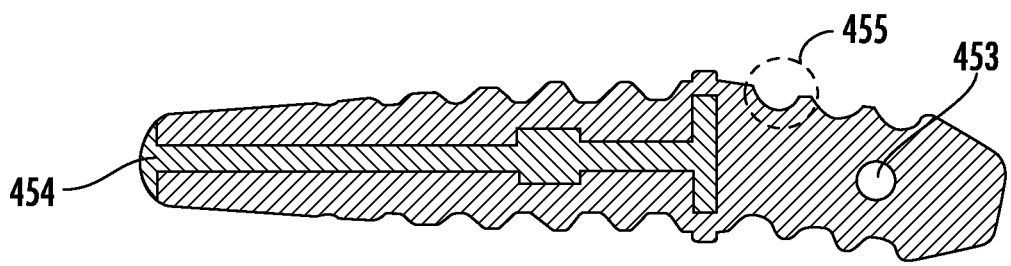
FIG. 24A is the section view A-A of FIG. 24.

FIG. 24 is a top view and section view of an eighth embodiment 450 of an implant having a core member 454. Implant 450 has other features and advantages of the current invention as described herein. The core member 454 is shown in the proximal end 451 of the implant but may also extend into or be partially or entirely within the proximal end 452. The core member 454 may provide additional strength to implant 450. For example if the implant 450 is comprised of PEEK or another plastic or biocompatible material or a resorbable material or bone, it may be advantageous to have a core member 454 comprised of a stronger material such as nitinol, stainless steel, titanium or other biocompatible material. The core 454 would be relatively stronger than the surrounding implant material. This may be particularly advantageous for enhancing the strength of smaller implants and may provide a means for creating bone engaging features on implants of small size with enhanced core strength. The core may also provide the benefit of being radio-opaque.

Figure 25:
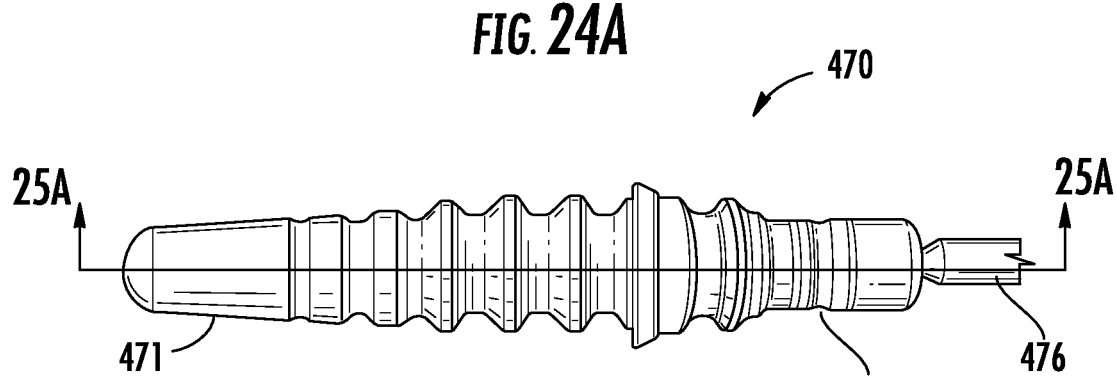
FIG. 25 is a top view of a ninth embodiment depicting a design of the invention with a core member extending completely through the implant.
Figure 25A:
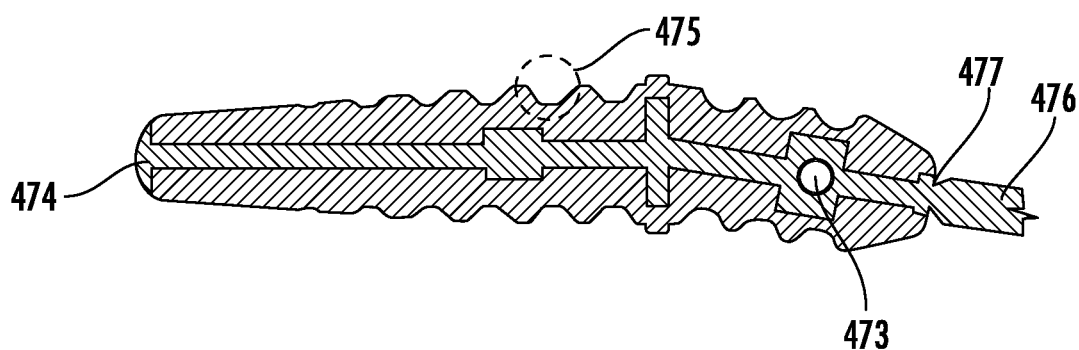
FIG. 25A is the section view A-A of FIG. 25.

FIG. 25 is a top view and section view of a ninth embodiment of the invention, implant 470. Implant 470 has a core member 474 and may have other features and advantages of the current invention as described herein. The core member 474 is shown extending completely through the implant 470 and incorporates the through hole 473. The core member 474 may provide additional strength to implant 470. For example, if the implant 470 is comprised of PEEK or another plastic or biocompatible material or a resorbable material or bone, it may be advantageous to have a core member 474 comprised of a stronger material such as nitinol, stainless steel, titanium or other biocompatible material. The core 474 would be relatively stronger than the surrounding implant material. The core may also provide the benefit of being radio-opaque. Having a core extend completely through the implant 470 would provide a driver end 476 that is releaseably attached to the implant 470. Implant 470 may be releaseably attached to driver end 476 such that after implantation the driver end 476 may be snapped or broken off. The implant 470 has a proximal end 471 and a distal end 472. The implant 470 may have bone engaging features 475 and or a through hole 473 as previously described herein. As depicted in FIG. 25, implant 470 has a core member 474 that is attached at one end to a driver 476. As shown, the attachment 476 is at the distal end 472 of implant 470 but may also be at the proximal end 471 depending on the intended use of the device. The attachment means 477 will be of a geometry that will allow transfer of sufficient force and manipulation for insertion while allowing the driver end 476 to be removed by either breaking, snapping or cutting the connection attachment means 477. This may be advantageous to allow the implant and inserter to be manufactured by low cost processes such as injection molding or over molding. This may reduce the cost of the device and may provide for additional recycling of the driver material. This may be further advantageous in reducing surgical complexity and or surgical time.

Figure 26:
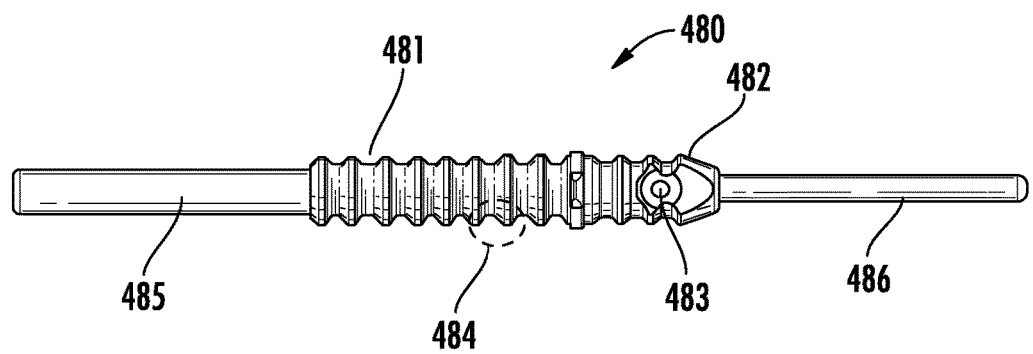
FIG. 26 is a side view of a tenth embodiment of the invention depicting an implant with extended ends.

FIG. 26 is a side view of implant 480. Implant 480 may have a proximal end 481 and a distal end 482. Implant 480 may also have bone engaging means 484 and or a through hole 483 as well as other features and advantages of the current invention as described herein. Implant 480 may also have an extended proximal end 485 and or an extended distal end 486. Extended ends 485 and 486 may be trimmed at the time of use to create a specific size. The extended ends 485 and 486 may be smooth or may have other features as described herein.

Figure 27:
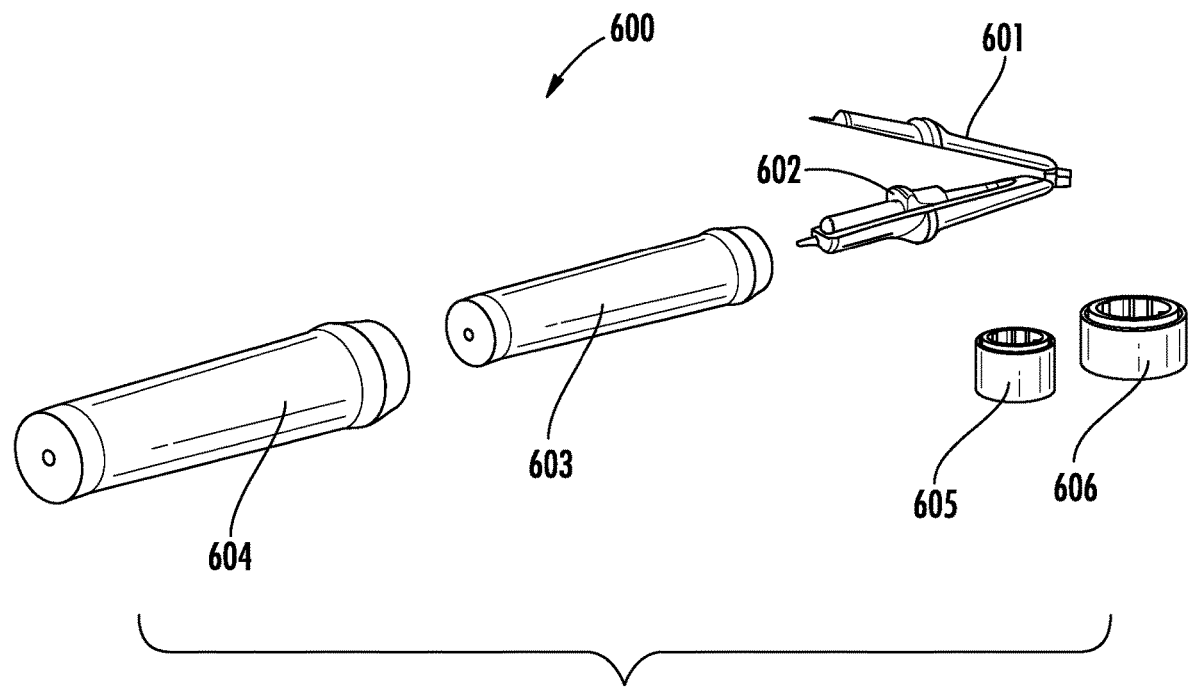
FIG. 27 is an exploded view of an alternate embodiment of a kit of the invention with the implant pre-assembled to an inserter in a sterile package.

FIG. 27 is an exploded view of an implant kit 600 that may have an implant of the current invention as described herein pre-assembled to an insertion or driver device 602. The assembly of the inserter/driver and implant may be contained in a clamshell or other holding device 601. The assembly of the inserter/driver and implant may be sterile packaged.

The descriptions of the implants, instruments, and surgical technique embodiment and configurations described herein are not limiting. Based on the description herein, those skilled in the art will understand that there are numerous configuration and or embodiments that will be within the scope of the current invention. The exemplary embodiments described herein are not intended to be limiting.

What is claimed is:

1. A method of implanting an implant for osteosynthesis of first and second bone segments, comprising the steps of:
    providing the implant, wherein the implant comprises an implant body and a suture;
    wherein the implant body is elongated along a first direction between a first end and a second end opposite the first end, wherein the first end comprises a first maximum outer dimension in a plane that is perpendicular to the first direction and a first bone engaging feature, wherein the suture is attached to the first end, wherein the second end comprises a second maximum outer dimension in the plane and a second bone engaging feature;
    wherein the implant body comprises a stop feature and a key, wherein the stop feature is interposed between the first and second ends and extends outwardly beyond the first and second maximum outer dimensions to prevent over-insertion of the first end into the first bone segment or the second end into the second bone segment, wherein the key extends unilaterally outwardly from the stop feature;
    arranging the implant in a surgical site comprising the first and second bone segments and then affixing the implant in the first and second bone segments, wherein the implant is arranged partially or fully in an intramedullary canal;
    wherein when the implant body is in its final implanted position relative to the first and second bone segments, the stop feature is interposed between the first and second bone segments.

2. The method of claim 1, wherein the first end of the implant body comprises a through hole for receiving the suture.

3. The method of claim 1, wherein the implant is adapted to fuse a joint.

4. The method of claim 1, wherein when the implant body is in its final implanted position relative to the first and second bone segments, the key engages the first and/or second bone segments to resist rotation of the implant body relative to the first and/or second bone segments.

5. The method of claim 1, wherein providing the implant comprises providing a sterile kit comprising the implant.

6. The method of claim 1, wherein when the first end of the implant body is placed into the first bone segment and the second end of the implant body is placed into the second bone segment, the suture extends through the first bone segment and pulls the first bone segment toward the second end of the implant body.

7. The method of claim 4, wherein the implant body comprises a first relatively flat surface extending along a first side of the implant body.

8. The method of claim 1, comprising the steps of:
    attaching the suture to the first end of the implant body;
    passing the suture through the first bone segment;
    placing the first end of the implant body in the first bone segment;
    placing the second end of the implant body in the second bone segment; and
    tightening the suture to bring the first and second bone segments together.

9. The method of claim 8, wherein the first and second bone segments each comprise a cortical shell having an internal boundary, wherein the profile of the implant fits within the internal boundaries of the cortical shells of the first and second bone segments.

10. The method of claim 8, wherein when the first end of the implant body is placed in the first bone segment, the suture extends from the first end of the implant body through the first bone segment away from the second end of the implant body substantially along the first direction.

11. A method of implanting an implant for osteosynthesis, comprising the steps of:
    providing the implant, wherein the implant comprises an elongated body comprising a first end, a second end opposite the first end, an intermediate feature between the first and second ends, and a key protruding transversely from the intermediate feature;
    wherein the first end has a first maximum major diameter, a first bone engaging feature, a first relatively flat surface extending along a first side of the implant, and a transverse through hole that extends through the first relatively flat surface;
    wherein the second end has a second maximum major diameter and a second bone engaging feature;
    wherein the intermediate feature has a third maximum major diameter, wherein the key extends outwardly past the first, second, and third maximum major diameters; and
    a suture extending through the transverse through hole;
    passing the suture through a first bone segment;
    placing the first end of the implant body into the first bone segment;
    placing the second end of the implant body into a second bone segment, wherein the suture extends from the first end of the implant body through the first bone segment away from the second end of the implant body; and
    tightening the suture to pull the first bone segment towards the second end of the implant body.

12. A method of implanting an implant for osteosynthesis of first and second bone segments, comprising:
    providing the implant, wherein the implant comprises an implant body and a suture;
    wherein the implant body is elongated along a first direction between a first end and a second end opposite the first end, wherein the first end comprises a first maximum outer dimension in a plane that is perpendicular to the first direction and a first bone engaging feature, wherein the suture is attached to the first end, wherein the second end comprises a second maximum outer dimension in the plane and a second bone engaging feature;

wherein the implant body comprises a stop feature and a key, wherein the stop feature is interposed between the first and second ends and extends outwardly beyond the first and second maximum outer dimensions to prevent over-insertion of the first end into the first bone segment or the second end into the second bone segment, wherein the key extends unilaterally outwardly from the stop feature;

attaching the suture to the first end of the implant body;

arranging the implant in a surgical site comprising the first and second bone segments;

passing the suture through the first bone segment;

placing the first end of the implant body in the first bone segment;

placing the second end of the implant body in the second bone segment;

affixing the implant in the first and second bone segments; and tightening the suture to bring the first and second bone segments together;

wherein when the implant body is in its final implanted position relative to the first and second bone segments, the stop feature is interposed between the first and second bone segments.

13. The implant of claim 12, wherein the first end of the implant body comprises a through hole for receiving the suture.

14. The implant of claim 12, wherein all or a portion of the implant is adapted to be implanted in an intramedullary canal.

15. The implant of claim 12, wherein the implant is adapted to fuse a joint.

16. The implant of claim 12, wherein when the implant body is in its final implanted position relative to the first and second bone segments, the key engages the first and/or second bone segments to resist rotation of the implant body relative to the first and/or second bone segments.

17. The implant of claim 16, wherein the implant body comprises a first relatively flat surface extending along a first side of the implant body.

18. The method of claim 12, wherein providing the implant comprises providing a sterile kit comprising the implant.

19. The implant of claim 12, wherein when the first end of the implant body is placed into the first bone segment and the second end of the implant body is placed into the second bone segment, the suture extends through the first bone segment and pulls the first bone segment toward the second end of the implant body.

20. The method of claim 12, wherein the first and second bone segments each comprise a cortical shell having an internal boundary, wherein the profile of the implant fits within the internal boundaries of the cortical shells of the first and second bone segments.

21. The method of claim 12, wherein when the first end of the implant body is placed in the first bone segment, the suture extends from the first end of the implant body through the first bone segment away from the second end of the implant body substantially along the first direction.

* * * * *